United States Patent
Lee et al.

(10) Patent No.: US 8,335,551 B2
(45) Date of Patent: Dec. 18, 2012

(54) METHOD AND MEANS FOR CONNECTING A LARGE NUMBER OF ELECTRODES TO A MEASURING DEVICE

(76) Inventors: Chong Il Lee, Stanton, CA (US); Sergio Lara Pereira Monteiro, Los Angeles, CA (US)

( * ) Notice: Subject to any disclaimer, the term of this patent is extended or adjusted under 35 U.S.C. 154(b) by 594 days.

(21) Appl. No.: 12/586,562

(22) Filed: Sep. 24, 2009

(65) Prior Publication Data
US 2010/0079156 A1   Apr. 1, 2010

Related U.S. Application Data

(60) Provisional application No. 61/194,515, filed on Sep. 29, 2008, provisional application No. 61/198,029, filed on Nov. 3, 2008.

(51) Int. Cl.
*A61B 5/0478* (2006.01)
(52) U.S. Cl. ......... 600/377; 600/378; 600/393; 600/544
(58) Field of Classification Search .............. 600/377, 600/378, 393, 544
See application file for complete search history.

(56) References Cited

U.S. PATENT DOCUMENTS

| | | | | |
|---|---|---|---|---|
| 5,215,088 A * | 6/1993 | Normann et al. | | 600/377 |
| 6,038,480 A * | 3/2000 | Hrdlicka et al. | | 607/116 |
| 6,171,239 B1 * | 1/2001 | Humphrey | | 600/372 |
| 7,096,070 B1 | 8/2006 | Jenkins et al. | | |
| 7,212,851 B2 | 5/2007 | Donoghue et al. | | |
| 7,346,312 B2 | 3/2008 | Irazoqui-Pastor et al. | | |
| 8,000,804 B1 * | 8/2011 | Wessendorf et al. | | 607/116 |
| 2003/0120328 A1 * | 6/2003 | Jenkins et al. | | 607/116 |
| 2004/0133118 A1 * | 7/2004 | Llinas | | 600/544 |
| 2010/0082076 A1 * | 4/2010 | Lee et al. | | 607/17 |

OTHER PUBLICATIONS

Fiaccabrino, et al. "Array of Individually Addressable Microelectrodes" in Sensors and Actuators B: Chemical; 19 (1994) pp. 675-677.*
Scott J. Cruikshank and Barry W. Connors "Neuroscience: state-sanctioned synchrony" Nature vol. 454, pp. 839-840 (Aug. 14, 2008).
J.L. Reed, P. Pouget et al., "Widespread spatial integration in primary somatosensory cortex", Proc Natl Acad Sci USA, vol. 105, No. 29, pp. 10233-10237 (Jul. 2008).
James F.A. Poulet and Carl C.H. Petersen "Internal brain state regulates membrane potential synchrony in barrel cortex of behaving mice", Nature vol. 454, pp. 881-885 (Aug. 14, 2008).
Rachel J. Wilson, G.G. Turner and G. Laurent "Transformation of olfactory representations in the Drosophila antennal lobe", Science vol. 303, pp. 366-370 (2004).

* cited by examiner

*Primary Examiner* — Lee S Cohen
*Assistant Examiner* — Erin M Cardinal

(57) ABSTRACT

A picafina device that is an electrode for measurement of neuron electrical activity where the number of measurement points is very large, and methods of selecting a subset of available measuring electrodes on the surface of the device. The device can keep the selection for a predetermined length of time, or for an indefinite length of time, both under control of the researcher or the neurosurgeon. Selecting a different measuring pad, or a combination of pads, is equivalent to making measurement at a different location or on a nearby neuron. Several parallel measurements can be made, in which case correlations can be made between the firing of different neurons.

8 Claims, 17 Drawing Sheets

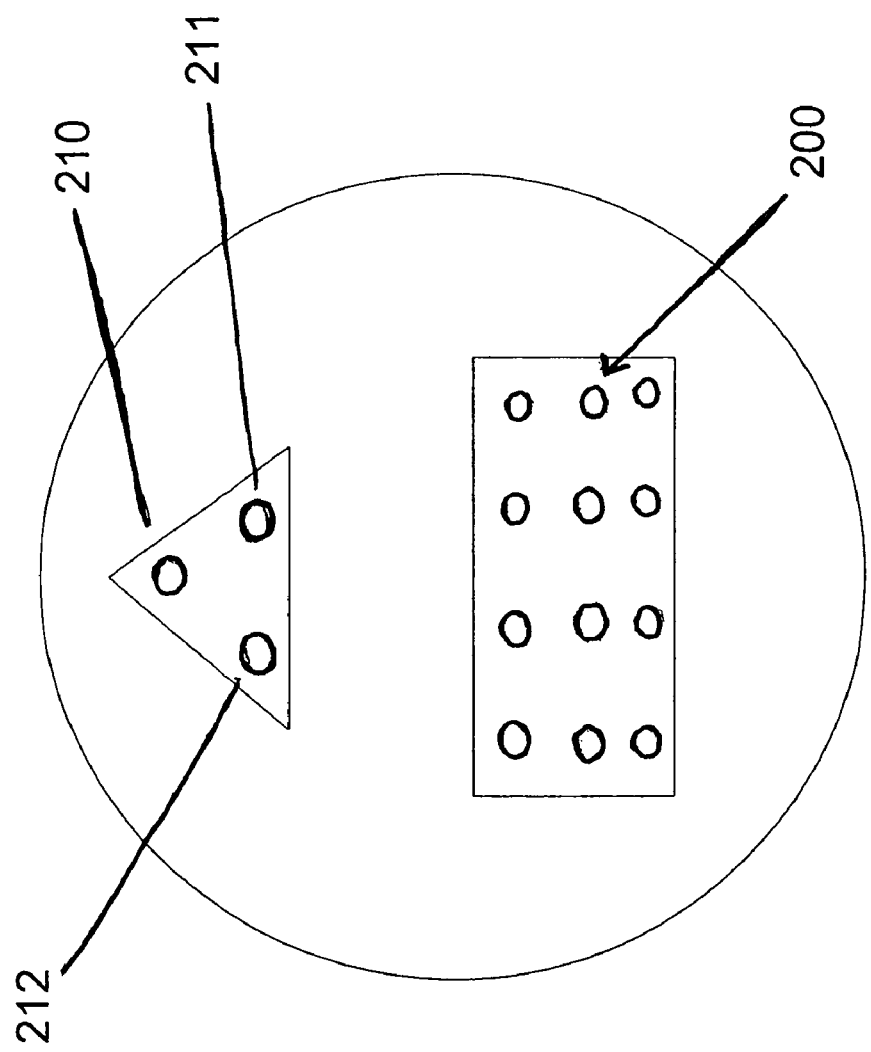

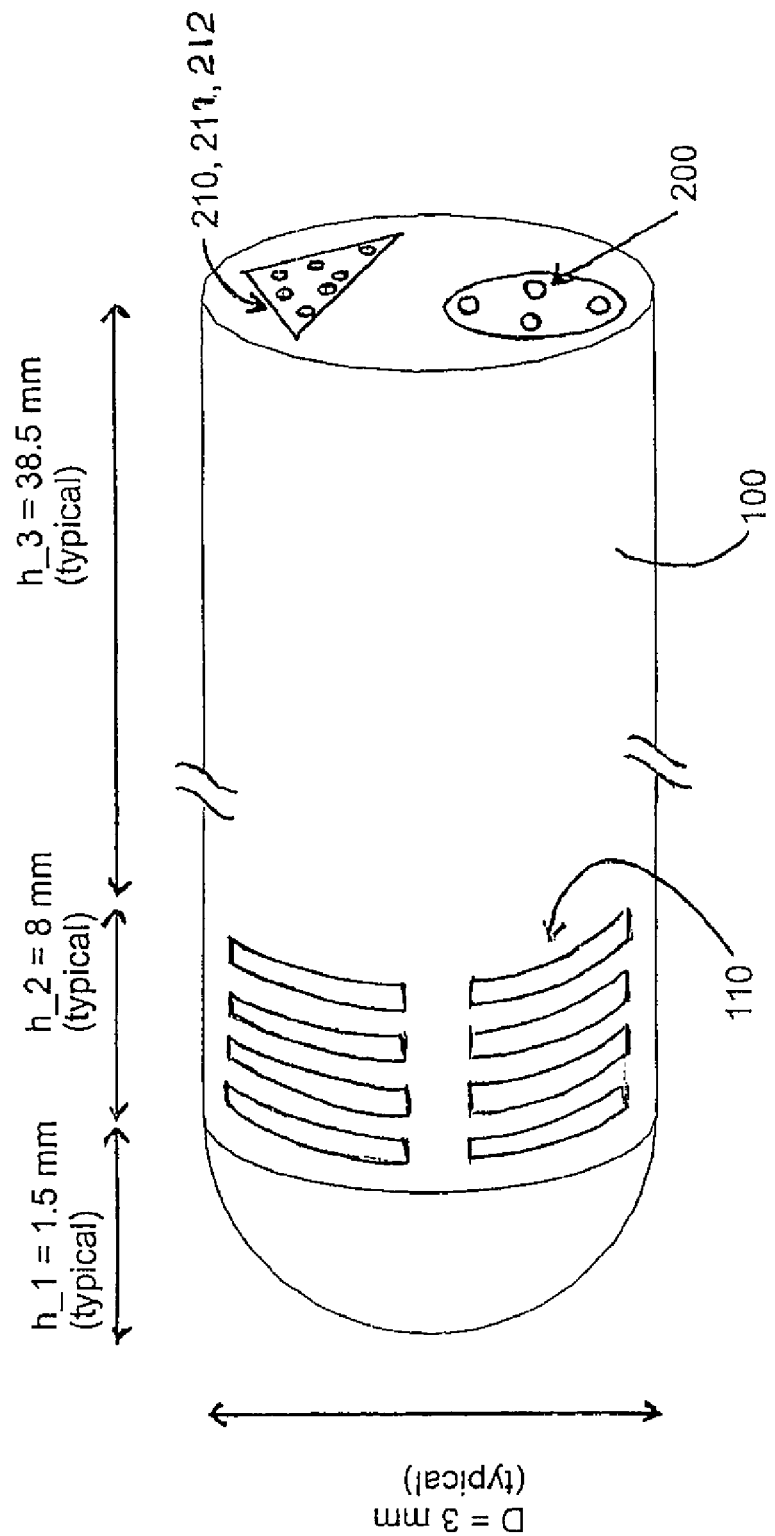

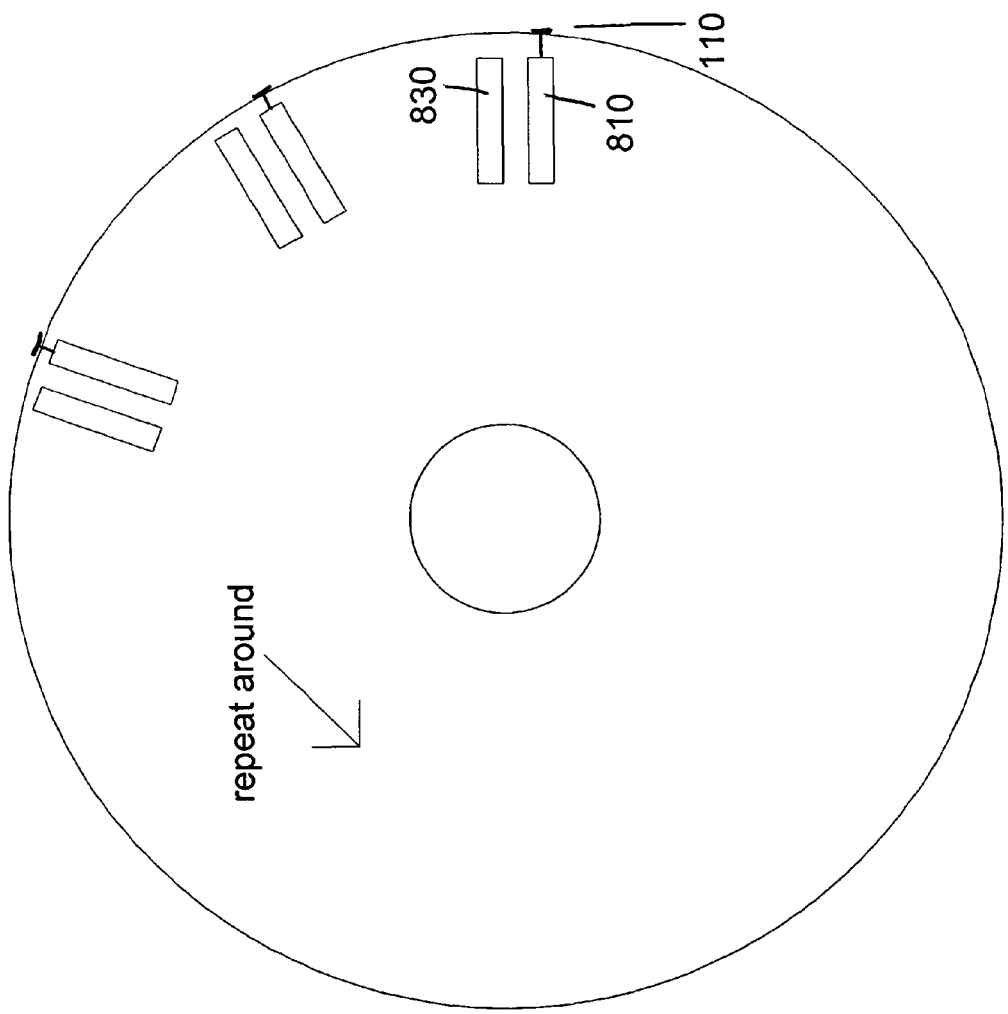

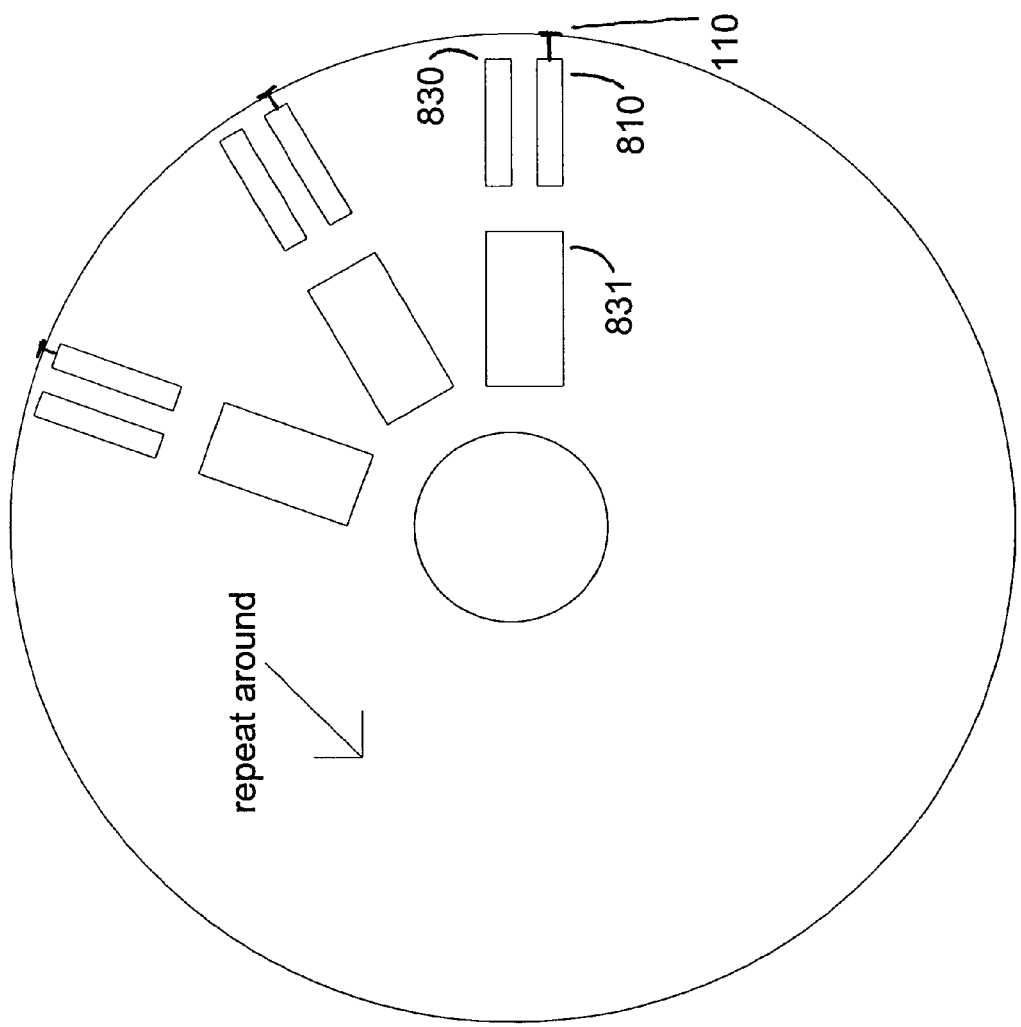

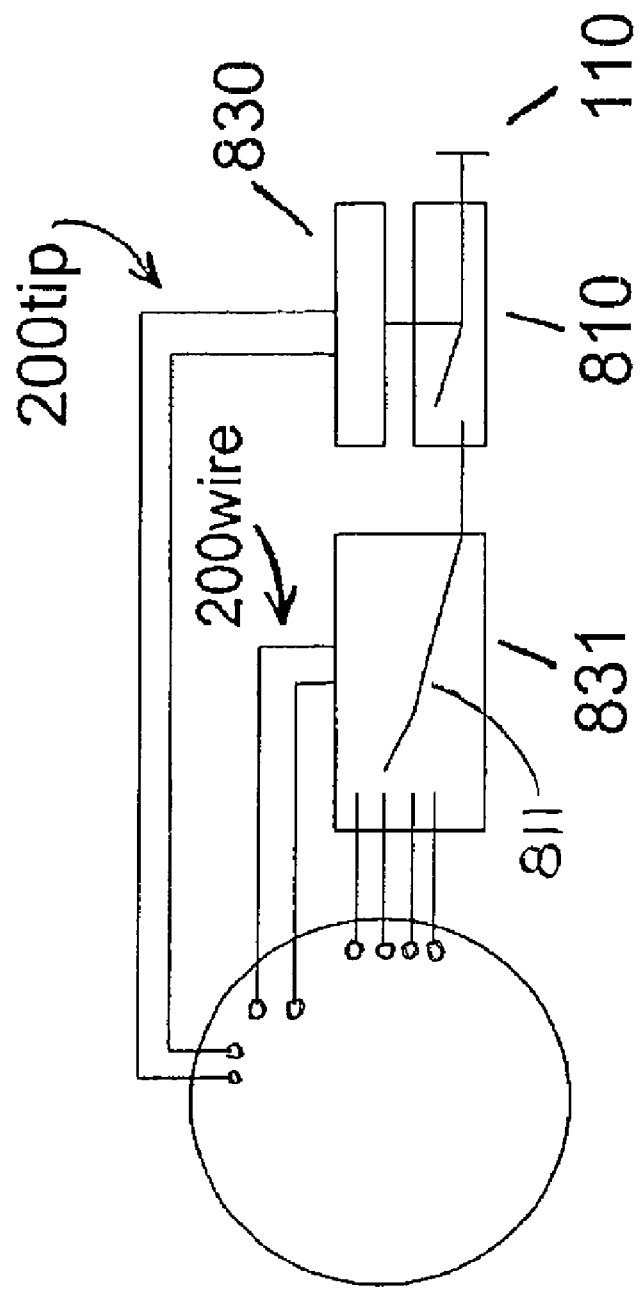

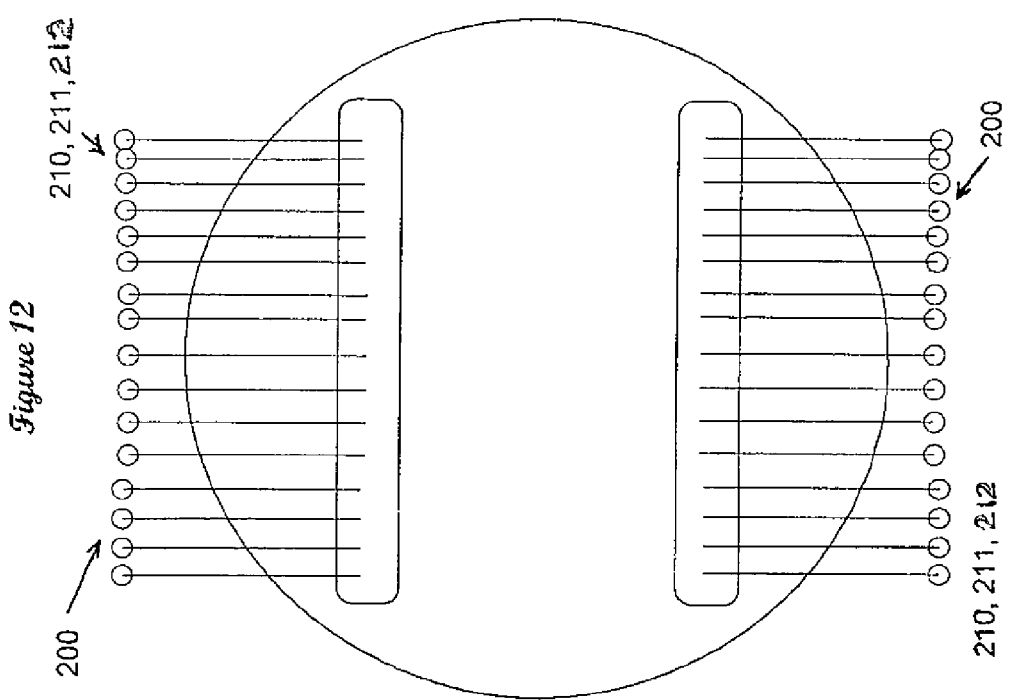

METHOD AND MEANS FOR CONNECTING A LARGE NUMBER OF ELECTRODES TO A MEASURING DEVICE

CROSS REFERENCES TO RELATED APPLICATIONS

This application is based on, and claims benefit of Provisional Application Ser. Nos. 61/194,515, filed Sep. 29, 2008; and 61/198,029, filed Nov. 3, 2008.

FEDERALLY SPONSORED RESEARCH

Not Applicable

SEQUENCE LISTING OR PROGRAM

Not Applicable

BACKGROUND OF THE INVENTION

1. Field of Invention

This invention relates to cellular electrical measurements in general, for animals, including humans, and neuron electrical measurements in particular.

2. Definition of Terms

To assert. In digital electronics it means to make a wire on or off, as needed, or a set of wires to be in any combination on and off, as needed. In this context "on" an "off" generally mean one of the two possibilities of a binary representation, as on=5V, off=0V, on=magnetic field up, off=magnetic field down, on=light, off=dark, etc.

B/H/D after a number, or in subindex, stands for binary/hexadecimal (hex)/decimal number representation. For example: 1010B=0AH=10D Bus. A set of wires grouped according to its function. For example, the address bus is the set of wires which carries the address value for something, the data bus is the set of wires which carries the data, or numerical value for something.

Demultiplexer. A type of electronic switch with a single input and a plurality of outputs, also with a number of binary inputs capable of creating a binary address which can select which of the outputs will be connected to the single input (cf. multiplexer). The device of our invention uses a demultiplexer capable of also latching the output selection, that is, a demultiplexer that maintain the connection between the single input and the selected output even after the address is out from its address port (it latches), or even if the address changes to another value.

Integrated circuit. As used herein, the term "integrated circuit" refers to a small-scale, electronic device densely packaged with more than one integrated, electrical component. The components are manufactured on the surface of semiconductor material. There are various scales of integrated circuits that are classified based on the number of components per surface area of the semiconductor material, including small-scale integration (SSI), medium-scale integration (MSI), large-scale integration (LSI), very large-scale integration (VLSI), ultra large-scale integration (ULSI)

Latch. A term used in digital electronics meaning the capability to keep some particular configuration, or output, or logic, or selection, even after the selecting source, etc., is no longer active, or even if the selecting source is changed to a different value. Another way to look at it is that a latched device has memory to keep a configuration when instructed to do so. A standard wall light switch is an example of a latch because it keeps the last state it was set by a human being, either on or off.

Measuring tip. The very tip of the measuring wire, sometimes referred as electrode in current art, made of metal or some other electrically conducting material. In current art devices the measuring tip is generally at the end of a thin, stiff wire, typically 100 micrometers diameter, separated by 100 micrometers, or more, while in our invention the measuring tip is a metallic area as small as a few micrometers, typically 5 micrometers but can be less or more according to the need, separated by as little as 5 micrometers, at the surface of the device of our invention. Current art is capable of manufacturing measuring tips for our invention that are less than one micrometer in diameter, and the shape is not necessarily circular.

Multiplexer (MUX) a type of electronic switch with a plurality of inputs and one single output, also with a number of binary inputs capable of creating a binary address which can select which of the inputs will be connected to the single output. (cf. Demultiplex).

Neural sensor. As used herein, the term "neural sensor" means an implantable device for sensing neural signals. Examples of neural sensors include microwire electrode arrays, optical sensors, microwires, magnetic field detectors, chemical sensors, and other suitable neural sensors which are known to those of skill in the art upon consideration of the present disclosure.

Picafina. A supporting structure used by the main embodiment of our invention, generally similar to the devices used in Deep Brain Stimulation but potentially with far more tips or electrodes than DBS devices, which is strong enough to allow it to be inserted in the brain or other body structures, and which contains the necessary wires for connecting the measuring tips and the address decoders with the controlling and measuring instruments. For use human animals, he dimension of a type I picafina is approximately the size of a wide drinking straw (5 mm.), its length being the necessary to reach the desired depth in the body. For smaller animals (as a mouse), the picafinas would be accordingly smaller, both in diameter and length, while for larger animals (as a whale or an elephant), the picafinas would be accordingly larger.

3. Short Introduction to the Art

It is well established that the neuron signals are electrically propagating signals. The roots of this fact can be traced at least to the Italian Luigi Galvani as early as 1771 with his famous frog's leg experiment.

This neuronal (electrical) traffic travels in both directions, from either the brain or intermediate neurons to the muscles or other body parts, or from sensory organs (skin, taste buds, vision rods and cones, etc.) to either other intermediate neurons or the brain. Measuring these signals is of importance for at least two reasons: such measurements may give us a clue of how the brain works; they may also help us to develop electrical actions on the nerves and on the brain to do things as to stop pain or to stop Parkinson's disease tremor or to stop epileptic seizures, etc. Accordingly, much effort has been put into devices to measure the neuronal electrical activity. Eric Kandel (Kandel (2000)) gives a good overview of the current state of the art from the academic point-of-view, while Miguel Nicolelis (ed.) (Nicolelis (2008)) gives a current review of the electrodes measuring devices directly related to the our invention here disclosed.

Accordingly, to measure the neuronal electrical activity, several measuring electrodes, or probes, or measuring pads, or measuring tips, henceforth most often referred to as "measuring tips" or simply "tips" have been developed.

The single tips used in the early days of the art have given place to multiple tips, and the sizes of said tips is much smaller in current art. These multiple tips have a double objective. One is to make simultaneous measurements, both to collect more data, as well as to investigate the correlation between the firing of different neurons. A second objective is associated with the widely known difficulty of accurately positioning said tips with its distal end at the precise area of interest, at a precise position relative to any neuron, say, close to a synapse, or to a particular neuron. With multiple tips, one of them, by chance, may happen to be near one of the areas of interest, so supporting devices with several tens, or even over one hundred tips have been introduced. Yet, in spite of the recognized need of better adjustment of the measuring point, no real solution has been offered to this known problem: how to have a very large number of reading positions on the area studied, for example a brain (or a spinal cord, or some nerve bundle going to or from a finger, etc.). A device with more measuring tips, capable of measuring more points, and also points that are closer to each other is needed. Note also that the multi electrode arrays of current art cannot select a position a few micrometers near a particular position, but only the other electrode at the end of another wire, that, because it is separated by a supporting structure, can hardly be less than 100 micrometers away. It follows that current art can only make measurements at points which is too far for the small synapses that may measure just a few micrometers. The advantage, or even necessity, of having a larger number of electrical tips to serve as electrical measuring points is known in the community, yet, despite much interest and work devoted to it, no solution was ever proposed to this known problem. Indeed, given the picafina diameter limitations, there is an intrinsic limitation on the number of wires that can be carried inside it, which in turn sets a limit on the number of possible tips on its surface or so is accepted by current art. The small number of tips (electrical contacts) has been one of the recognized problems associated with the art, a problem which has never solved even though much effort has been put to its solution. This is a problem that has been crying for solution for a long time. This is the problem addressed and solved by our invention.

Our invention is a picafina with a much larger number of tips than the current art devices, potentially of the order of many thousand tips. Besides disclosing a device with such a larger number of tips, our invention discloses a method to bring out the voltage values, without which the small diameter of said picafinas would not allow such large numbers of tips to send out the measured values using dedicated wires, as dedicated wires to each tip would not fit inside current art picafinas which have to be as small as possible in order to minimize trauma to the animal.

4. Discussion of Prior Art

The measuring tips or electrodes, as it is said within the neurology community, or neuron measuring electrodes or tips, to be more precise, are in prior art made of small electrically conductive tips, physically attached to some supporting structure, which is usually small to be accommodated inside the body of a living animal (including humans). They can be viewed as neural sensors. This electrical measuring tip, or neural sensor, is connected as needed to some usually external measuring instrument (usually a voltmeter) after being amplified, this amplification often occurring still inside the animal at the probe location. The electric potential at the neuron site is of the order of microvolts to millivolts. Often the electrodes, or probe, or tip, or pad, are held by equipment to help the researcher or neurosurgeon to move the tip with micrometer precision, which is needed to position it in close vicinity to a neuron (Nicolelis (2008), ch 1, pgs 12-20)

The measuring tip has to be such that it can be placed substantially close to the intended neuron, usually of the order of a few micrometers or even a fraction of a micrometer distance. The measuring tip itself has to be of a size comparable with the physical size of the system that is producing the signals it is measuring, that is, of a size comparable with the size of a neuron, or else it will make contact with other nearby systems, measuring averages from several neurons at the same time. This means that the measuring tip has to have a size on the order of one to a few tens micrometers in diameter, if it is to measure an individual neuron. There are probes intended to measure a group of neurons, and these can be larger.

Examples of multi electrode arrays in current use can be seen at G. Lehew and M. A. L. Nicolelis "State-of-the-Art Microwire Array Design for Chronic Neural Recordings" in Nicolelis (2008) pg. 1, where there are descriptions and photos of multi electrode arrays from 8 up to 128 electrodes or tips. The problem with these electrodes is that they are on individual, separated supporting wires, one wire for each tip, which increase the trauma on the animal, and prevent the electrodes from being less than 100 micrometers separation from each other. Scott J. Cruikshank and Barry W. Connors (Cruikshank (2008)) and James F. A. Poulet and Carl C. H. Petersen (Poulet (2008)) also discuss the needs, problems and current state of the art of multi electrodes measuring devices.

Some of the current art devices are the electrode manufactured by Alpha Omega Engineering (http://www.alpha-omega-eng.com/microelectrods/sma.asp) (Alpha Omega Engineering/PO Box 810/Nazareth Illit 17105/Israel/Tel 972-4-656-3327/Fax 972-4-657-4075/info@alphaomega-eng.com)

Many probes have several measuring tips, which allow concurrent measurements on several neurons. The multiplicity of tips also serves to adjust the exact point of measurement, because it is known to be difficult for the researcher (in a laboratory animal) or for the neurosurgeon (on a human patient) to position said measuring tip next to a particular neuron of such small dimensions. Ultimate measurement location is adjusted by selecting one or other (or several) of said tips or contacts. Tip selection is then made after insertion of the probe in the general area from which measurements are to be made, as the researcher, or the neurosurgeon, switch the measuring equipment from one tip to the next until, after having flipped through many tips that produce no signal or poor signal, he/she finds a tip that produces a good signal. There are also multi tips devices which allow each tip to be moved independently, usually forward and backwards only. Our invention offers an improvement on this change from one measuring tip to another, making it easier and more efficient. Our invention also allows the investigator or the neurosurgeon to make concurrent measurements on neurons closer together than previous art multi tip probes which have to be separated by the minimum distance of their supporting wires, which is of the order of 100 micrometers or more.

Irazoqui-Pastor (Irazoqui-Pastor (2008)) discloses an implantable device with multiple reading tips and a MUX (multiplexer), but he does not disclose a method and a means to have measuring tips that are very small and in very close proximity to each other (densely packed), in such a way as to cover a large area with selectable tips. In particular Irazoqui-Pastor does not disclose a system capable of combining the measuring tips together to make measuring areas of variable sizes, adjustable to the neuron size and location. And above all, Irazoqui-Pastor implicitly discloses an invention in which a large number of signal wires have to be brought to the MUX, a situation that forestalls a very large number of measuring tips in a small device. Nor did Irazoqui-Pastor disclosed a method to select a particular measuring tip then to keep it selected and to have a few selected together. Indeed, Irazoqui-Pastor disclosed the use of a MUX in the conventional way, which is in situations where space is not a problem. Because of these reasons, the invention disclosed by Irazoqui-Pastor fails to teach a method to allow a very large number of tips to be used, say, hundreds or thousands of tips, and accordingly, Irazoqui-Pastor does not mention the possibility of thousands of measuring tips.

Jenkins et al. (Jenkins (2006)) discloses a multiple tip system both for acquiring electrical signals and applying stimulation as well, but his invention is limited in that as disclosed, the number of measuring (or, stimulating) tips is limited, like all previous art electrodes, by the number of wires that can fit on the elongated body of the device. Superficially, Jenkins teachings is similar to mine, but without a very large number of individually addressable tips, the researcher cannot adjust precisely the location of measurement to be near one single neuron, and in this is the fundamental difference between his invention and mine. The need for a large number of contact tips has been recognized for a long time, and similar devices with multiple rings have been in use for Deep Brain Stimulation (DBS) (Medtronics (n/d)), but the constraint on the number of wires has kept the devices from advancing. Moreover, Jenkins failed to disclose the possibility of using the semiconductor manufacturing and printed circuit boards manufacturing techniques to achieve the smallest sized tips, what limits his tips to relatively large sizes.

Another example of modern prior-art devices is Donoghue et al. (Donoghue (2007)). His invention discloses a multi tip device, with each tip at the end of a small needle. Using this construction, the minimum separation of the tips is twice the size (diameter) of the supporting needle. Since the supporting needle can hardly be smaller than 50 micrometers, else it breaks, the distance between two reading electrodes is 100 micrometers minimum. Since 100 micrometers is much more than the size of a synapse in a typical brain neuron, it follows that this structure cannot adjust the measurement position with accuracies of the order of a fraction of the size of a neuron, as our invention can, and as it is needed.

Another examples of use of measuring devices are heart, muscle, pain carrying nerves, spinal cord etc.

OBJECTS AND ADVANTAGES

Accordingly, several objects and advantages of our invention are

1. The possibility of controlling a much larger number of electrical tips, or neural sensors, for measurements of electrical activity from a multiplicity of points, many more than in prior art, adding flexibility to the user 2. The possibility of controlling which said tips are on or off without using a dedicated wire to each said tips, because there is not enough room in the body of the supporting structure for many wires, 3. The possibility of housing and running through the picafina's limited space a smaller number of controlling wires from O&A (Objects and Advantages) #1, when a larger number of wires would be impossible to fit 4. The possibility of making measurements on brain neurons in insects, human and non-human animals. These deep brain locations control limb motion and may be involved in Parkinson's disease, epilepsy or other dysfunctions, so measurements may be necessary for diagnosis, while in research animals such places may be accessed for measurements for research purposes. FIG. 1 shows a perspective view of a basic version of our invention for a particular main embodiment used for deep brain measurements. For deep brain measurements the objective is to make measurements from parts of the brain that are deep inside the skull, as the thalamus.

Other objects and advantages are:

Thus one of the problems that this invention solves is how to make a very large number of electrical measuring tips on the surface of said picafina, in such a way that some of said measuring tips can be connected to an electrical measuring device, as a voltmeter, one at a time, or a few at a time, but using far less wires than the number of measuring tips.

Summing up, one of the objectives of this invention is to provide a physical means and a method to allow for a larger number of measuring tips than current art permit to have Further objects and advantages of our invention will become apparent from a consideration of the drawings and ensuing description.

SUMMARY

The invention is a method and a means to provide a large number of electrical tips from which to make measurements of the electric potential (voltage) at neurons and other cells of mammal animals, including humans, also of fishes, birds and even insects (Wilson (2004)).

Said measuring electrode tips at the end of said picafina, or electrical contacts at the distal end of the support, can have dimension as small as on the order of a fraction of or a few micrometers, and the distance between them can be similar in size too. If the picafina were inserted in the exactly desired position, that is, next to a neuron, then one single measuring tip would be all that would be needed. Unfortunately it is not possible for the surgeon to so precisely position the distal end of the picafina next to a neuron that he cannot see, in such a way that the measuring tip is next to a desired neuron. Moreover, the desired neuron is hard to locate, among other reasons due to the variety of inner brain (or any other tissue) structure from patient to patient. Indeed, though the relative position of all brain structures is the same on all patients, their physical size, and therefore their absolute position with respect to any fiducial mark is not the same. This is true for internal as well as external features: all humans have their noses above their mouths but their absolute distances measured from, say, the forehead, vary from individual to individual. In reality the distances are guaranteed to be different from individual to individual. It follows that the electrode positioning is less accurate than desirable. It is this intrinsic positional inaccuracy that is solved with our invention, which is a method and a means to handle extremely large numbers of measuring tips, which are positioned closer to each other than current art. With this large number of available measuring tips, the researcher or the neurologist can select the one that happens, by chance, to be at the desired location. All the electrodes in the main embodiment of the picafina of our invention make use instead of the same wire through a dedicated digital switch that can be turned on and off with a digital addressing system to select which measuring tip will be connected to said signal carrying wire. It is also possible to have a few wires to carry measurements out, in which case more than one measurement can be made simultaneously, and alternate embodiments of our invention disclose the possibility of multiple concurrent measurements. Such alternative embodiments are fitted with one address bus to select which measuring tip to use and a separate bus (a signal wire bus) to select which wire to use with the selected measuring tip. In one case or another, there are fewer wires out than there are measuring tips.

It would be from difficult to impossible to dedicate a wire to carry the voltage signal from each point-like, small electrode on the picafina, the difficulty increasing with larger number of measuring electrodes. The dilemma is that there is a need for a very large number of measuring tips, while there is no space for that many wires to carry out the measured voltage. The need for a large number of tips, or points from where to measure the voltage, exists because it is impossible to position the device with any accuracy next to a neuron that is unseen because the animal is alive (its body is working!), so that final placement adjustment is made by trial and error trying one (or a group) of tips until the best one(s) is (are) discovered. Sometimes several tips are used for simultaneous measurements too, useful to compare one with the other.

The need for such a large number of tips has been recognized for a long time (see Nicolelis (2008), preface Pgs. xiii to xv), and because the tips are much smaller than the wires connecting them to the outside measuring instruments, the limiting factor is the wire size. So, despite many attempts to make a large number of tips, never a solution was found of how to accommodate the large number of wires in the small space available, one wire for each tip, even if a common ground is used. Nor was ever a solution found for the need to keep the tips very close to each other. Current art offers tips that are approximately 250 micrometers apart, sometimes 100 micrometers separation, less than what researchers and neurosurgeons want. The first embodiment of our invention solves one part of this problem with the use of one single wire to carry the signal, which can then be connected to any of the large number of measuring tips after the picafina is in place. A second alternate embodiment of our invention goes further, with the option of a multiplicity of wires (2 sup 4=16, 2 sup 6=64, or more wires) that can be individually connected to as many measuring tips, offering the possibility of parallel measurements. Indeed, one of the obstacles encountered by current art (see Nicolelis (1998), Nicolelis (2008)) is that it becomes difficult to insert more than a few dozen or perhaps 100 wires in the brain or spinal column because of the potential damage to tissues, with the potential of eventually killing the animal. Our invention solves this problem of having a large number of measuring tips each of small size, while keeping a small number of connecting wires. The small size of the tips in turn allow for more precise choice of the location where the measurement is made.

DRAWINGS

Figure 1:
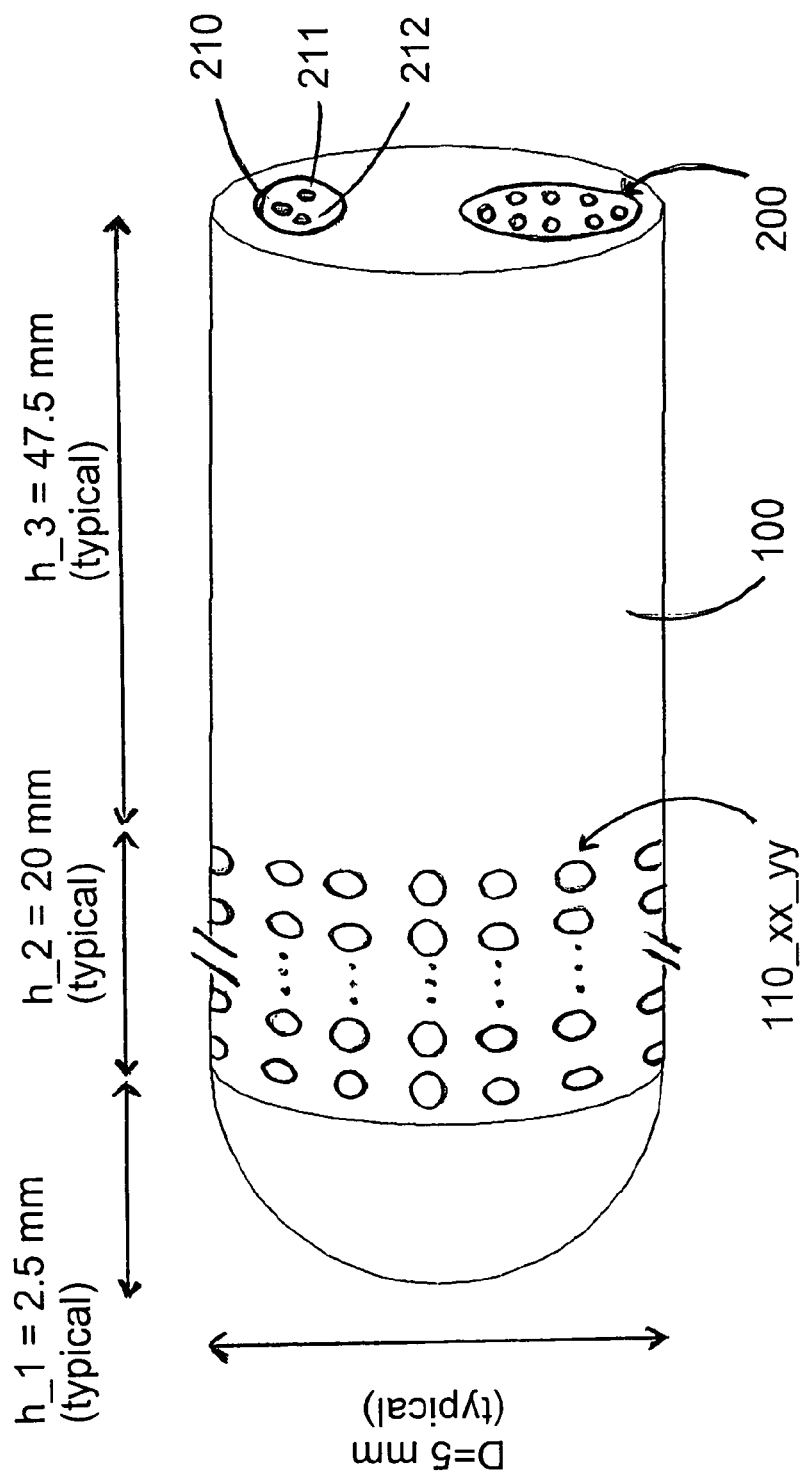
FIG. 1 shows an oblique view of a possible embodiment the picafina of our invention
Figure 2:
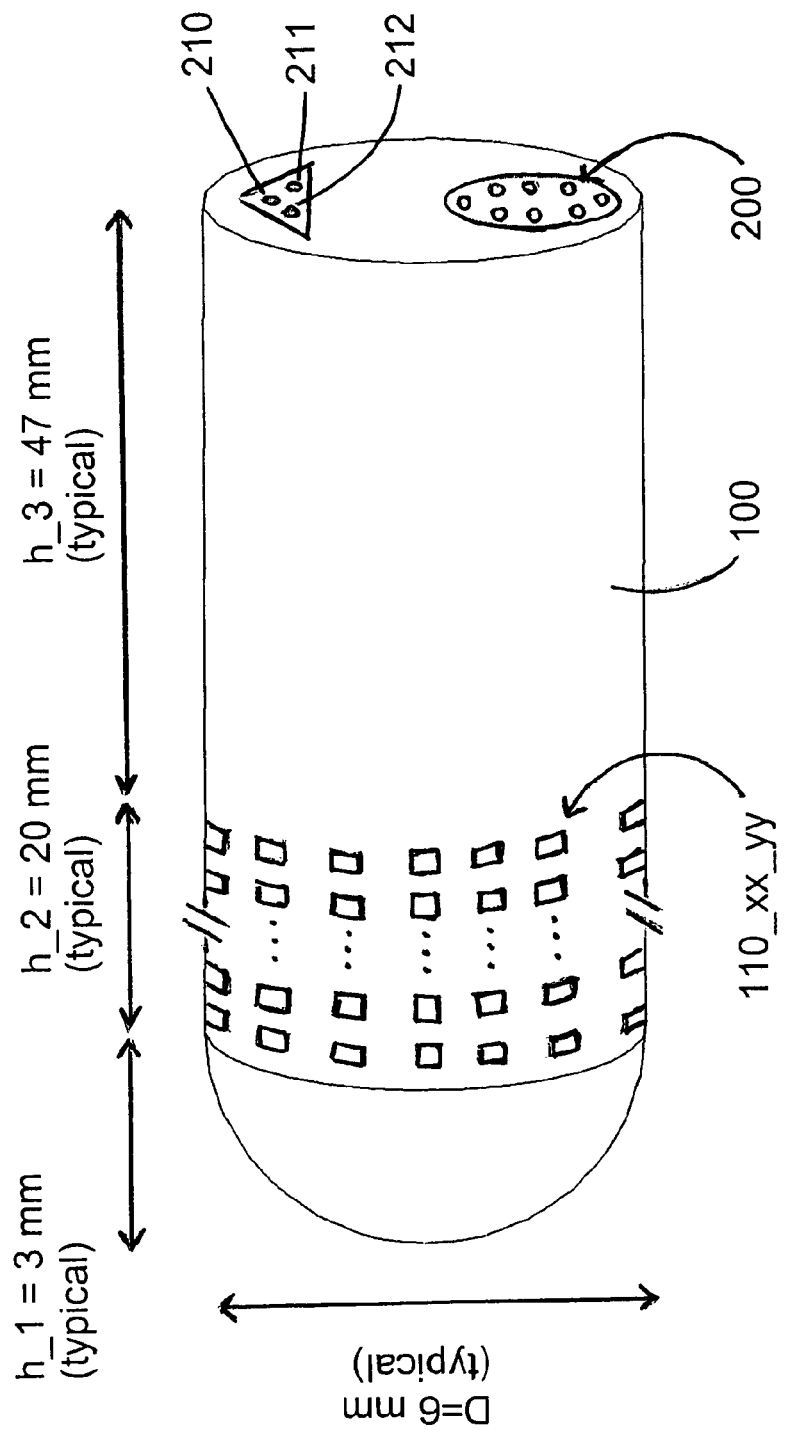
FIG. 2 shows the end of the picafina also with three rows of electrodes equally space as in FIG. 1 but with electrodes of a square shape.
Figure 3:
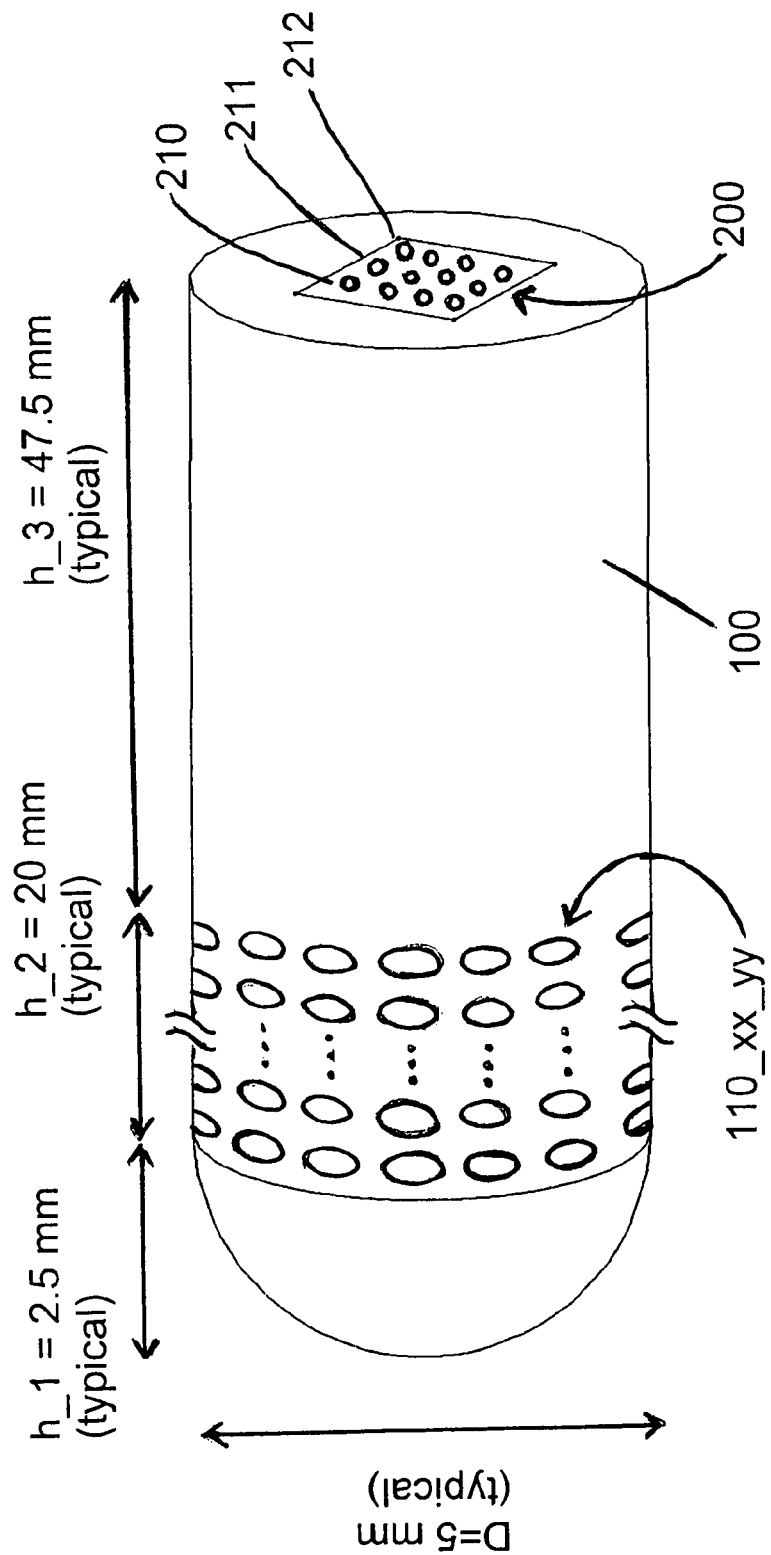
FIG. 3 shows the end of the picafina also with three rows of electrodes equally spaced as in FIG. 1 but with elongated electrodes along the circumference direction.
Figure 4A:
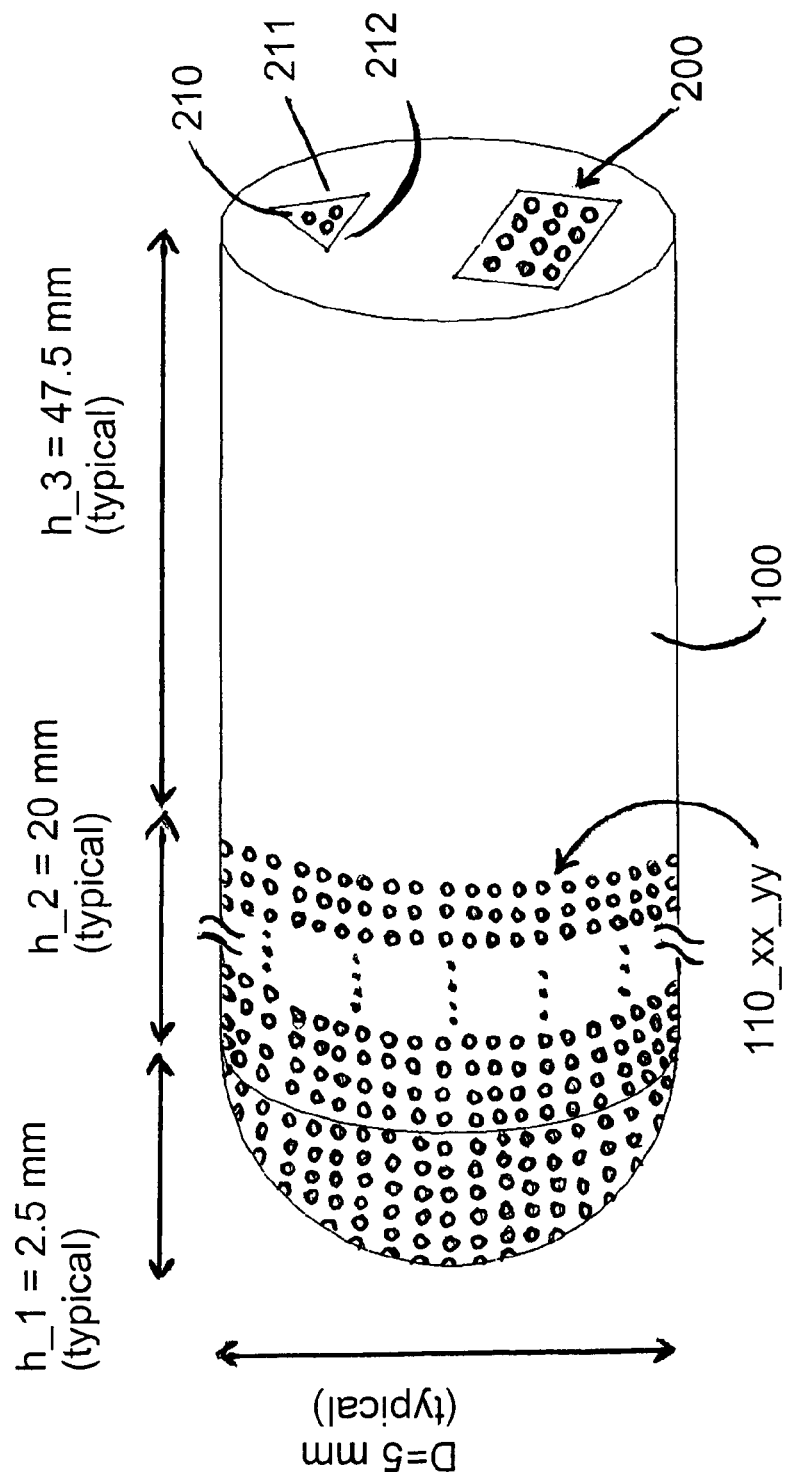

FIGS. 4a, and 4b, show another version of the picafina of our invention with a larger number of smaller electrodes for a larger electrode density as compared with FIGS. 1 through 3. FIGS. 4a, and 4b, depict a perspective view, and a proximal end view of this version. Cf with FIG. 10, which does not have pads on the concave tip of the distal end of the picafina. These are examples of modifications to adapt to particular needs, all within the scope of our invention.

Figure 5A:
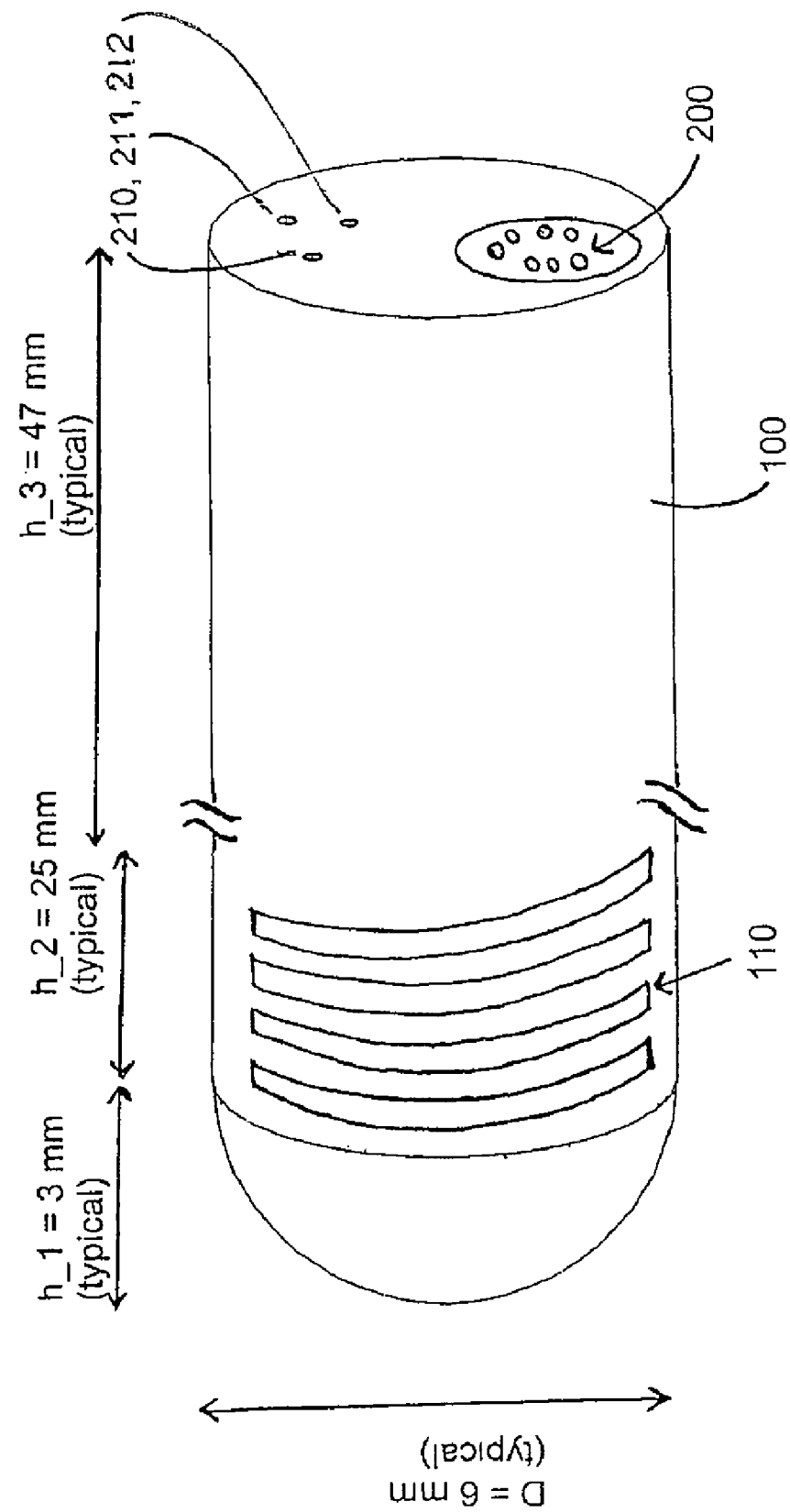

FIGS. 5a and 5b show variations on current art of picafina that can be implemented with existing technologies that allow a small number of electrical contacts.

Figure 6A:
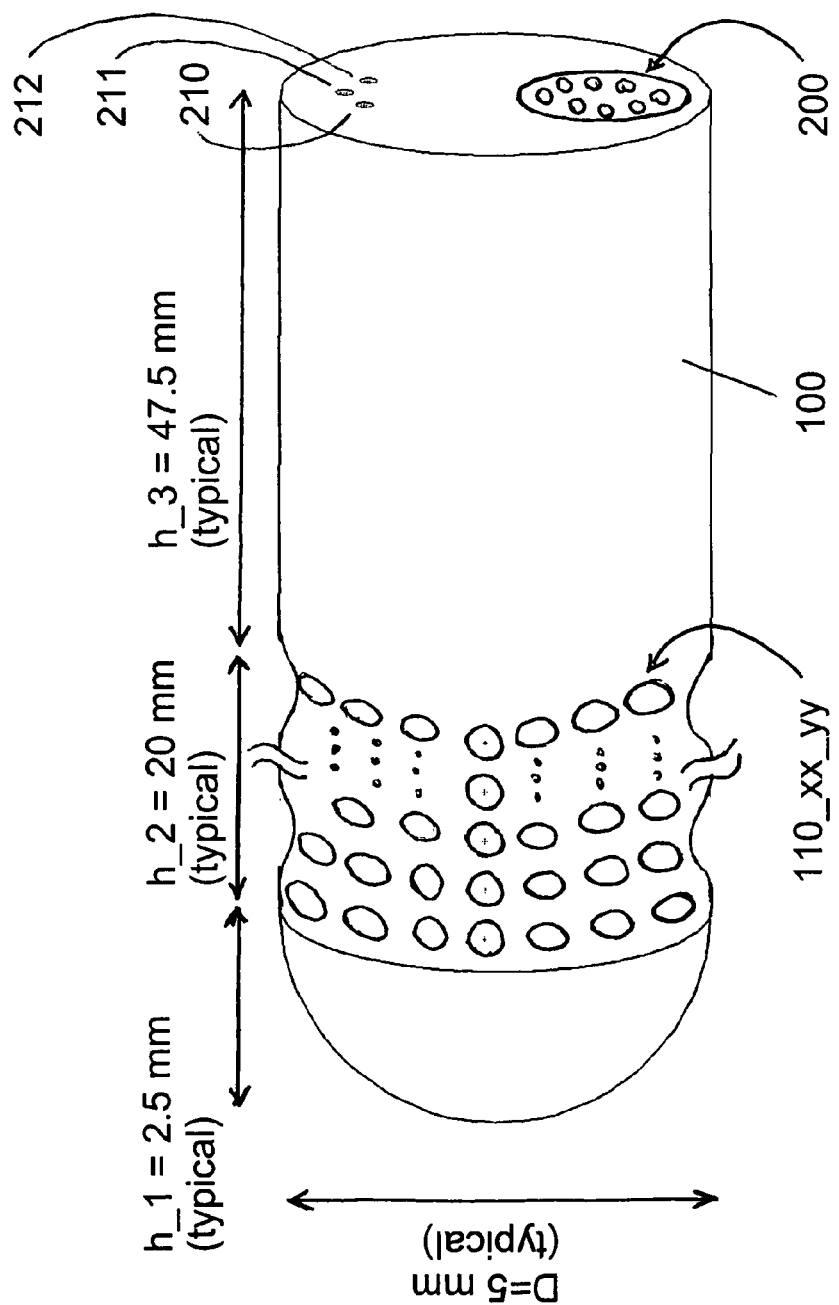
Figure 6B:
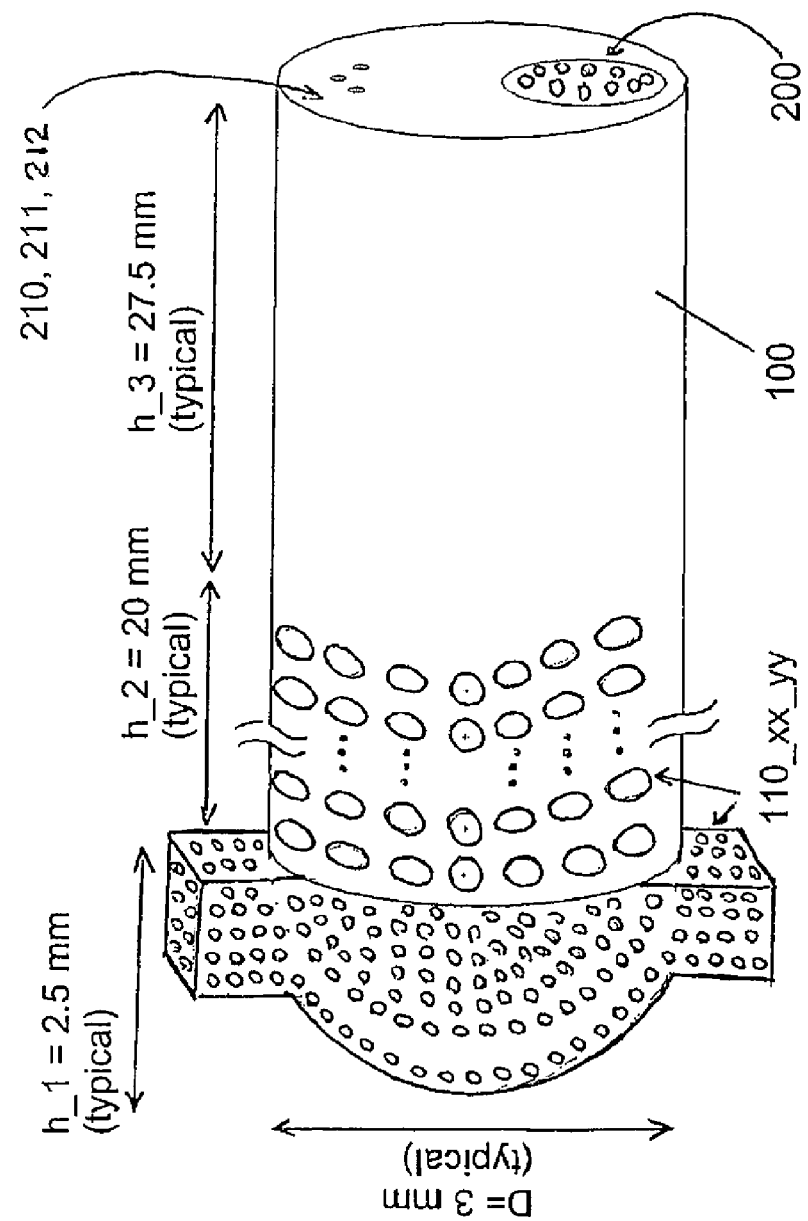

FIGS. 6a and 6b show an alternate profile for the picafina.

Figure 7B:
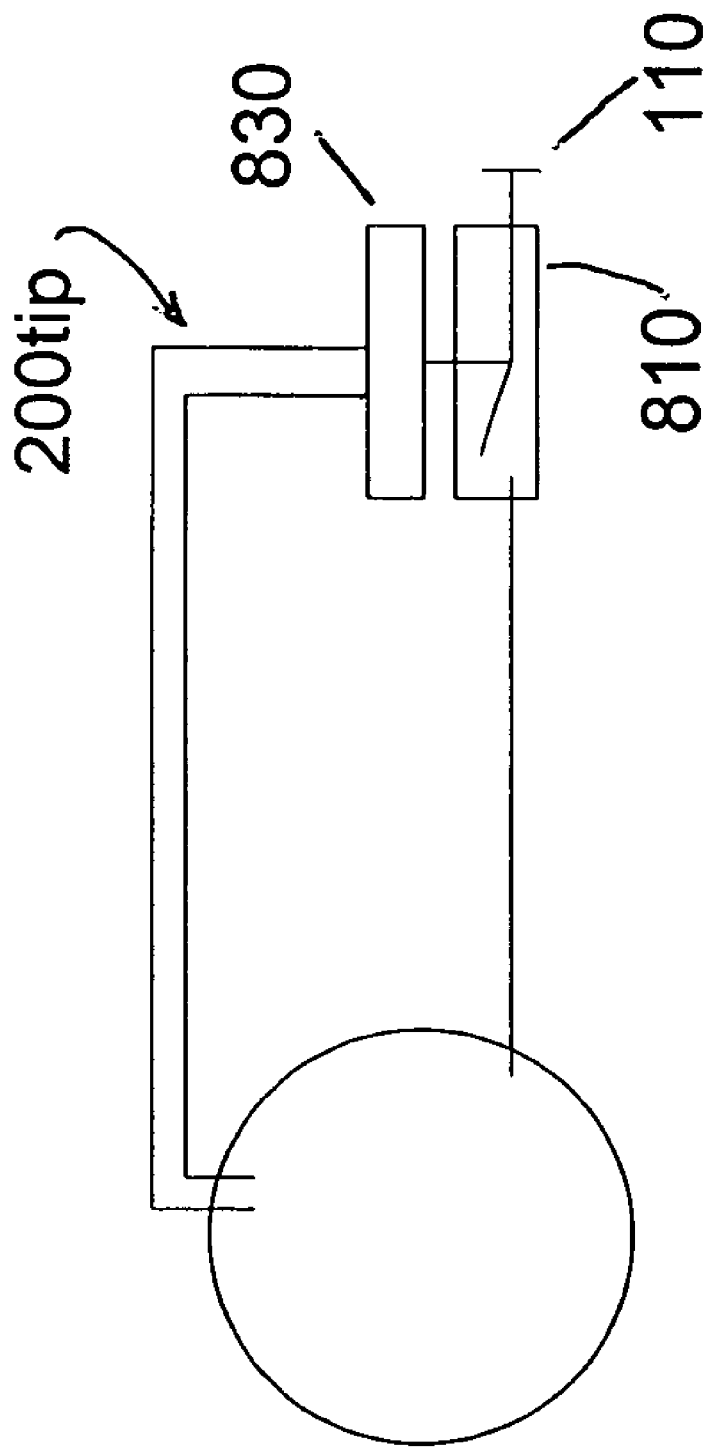

FIG. 7a and FIG. 7b show a block diagram of a possible electrical connection for the picafina of our invention laid on a picafina cross section perpendicular to its long, or z-dimension. Note that FIG. 8 is similar with the added multiplicity of measuring wires disclosed in the second embodiment. To avoid over-complication, only one of the measuring tips and its connections is shown in the cross section, similar circuits existing to serve each of the tips 110 at the surface of the device. Also to avoid over-complication, only three address lines are shown; typical devices use 8 and more address lines, to address 256 (2 power 8) measuring tips 110 and more. The ground wire can be connected to one or more of the tips 110, with similar circuits.

FIG. 8a and FIG. 8b show, in addition to the elements shown in FIG. 7, the added multiple measuring wires disclosed in a second embodiment. The physical lay-out of some of the similar electronic circuits that connect each of the tips on the surface of the picafina to the measurement wire that run inside the picafina along the z-direction. The tips shown are all at a particular fixed distance from either end of said picafina, or around a circular path on said picafina, as if along a ring on said picafina. Several such circuits are stacked along the longer dimension of the picafina (different z-coordinate), each serving to connect one of the tips that comprise that particular "ring" to the wire connecting to the measuring instruments. Each tip selector or address decoder 830 selects (on/off) a particular tip by its address. Once selected it is latched. Wire selector 831 selects which signal wire to connect according to address in 200wire. Once selected the result is latched. Latches not shown for simplicity.

Figure 9A:
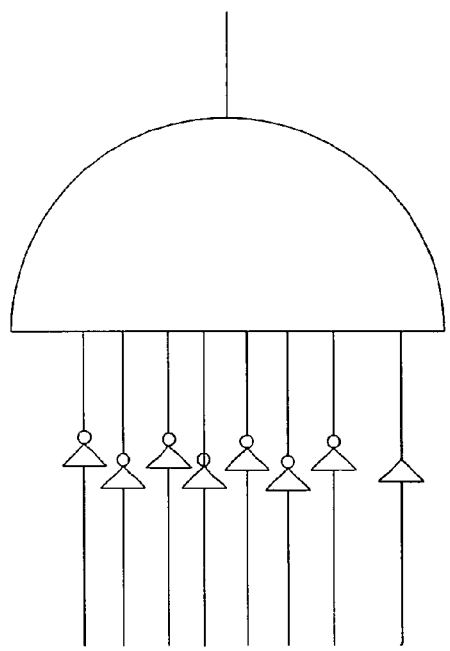
Figure 9B:
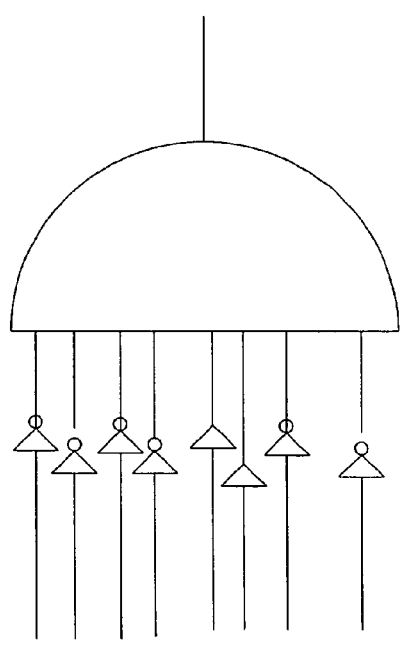

FIGS. 9a and 9b show two possible address decoders, (a) set to decode for the address 1 decimal=1 Hexadecimal=0000 0001 Binary, (b) set to decode for the address 12 Decimal=C Hexadecimal=0000 1100 Binary. Each address decoder has a different configuration of inverters, each different decoder associated with a measuring tip.

Figure 10:
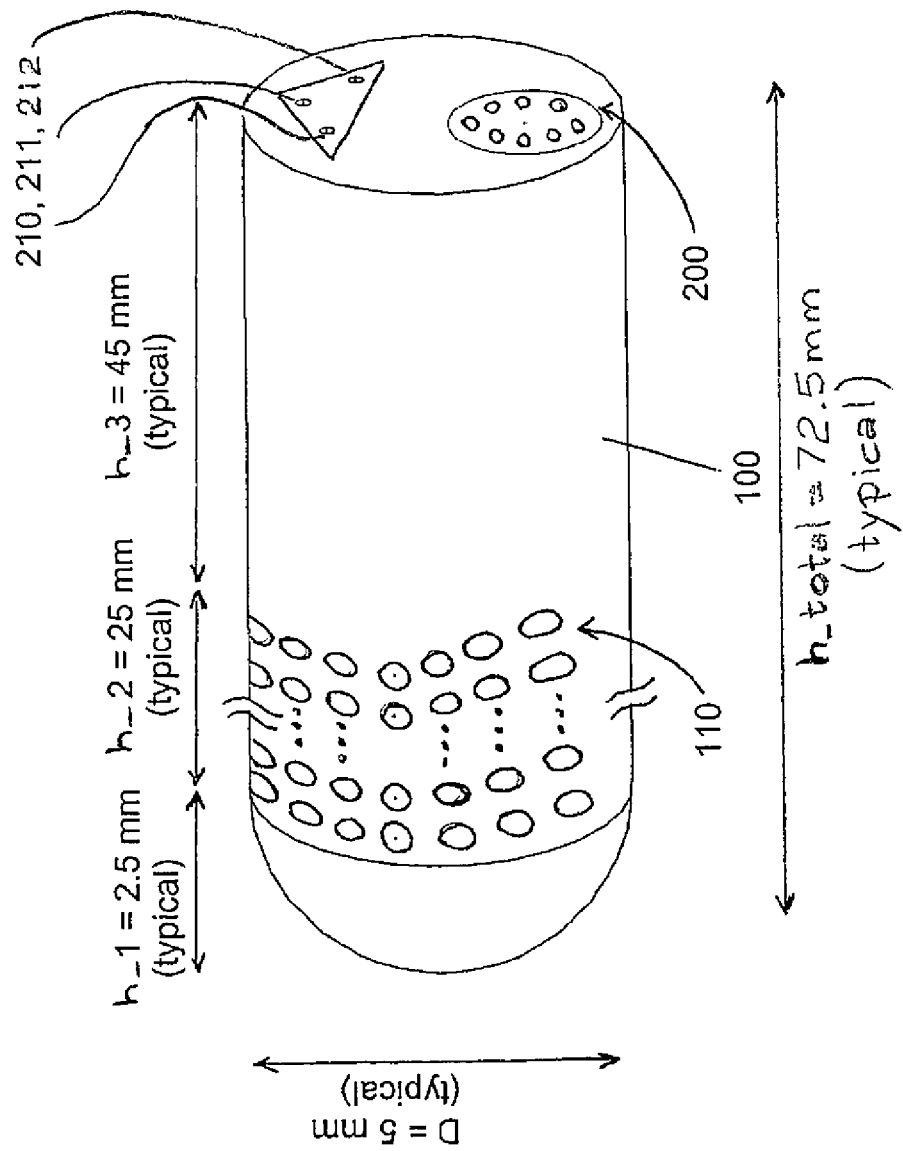

FIG. 10 shows a main embodiment of our invention with 12 electric tips or pads around the circumference of the picafina (or a "ring" of tips), 16 such "rings" and no electric tip on the concave extremity of the picafina.

Figure 11:
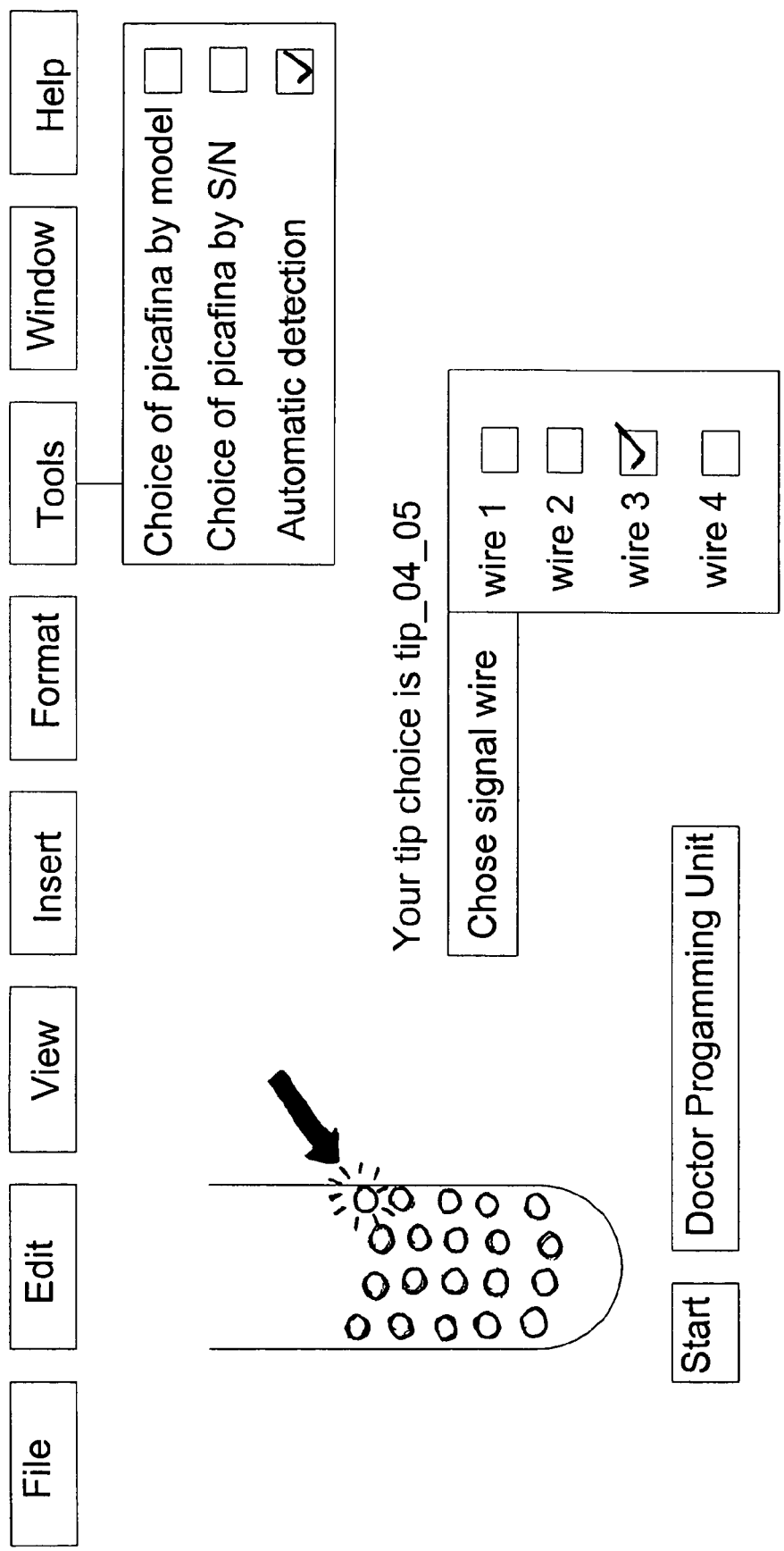

FIG. 11 shows a window environment with the drop-down menus for programming the Doctor's Programming Unit (DPU)

FIG. 12 shows a picafina with redundant wires at its proximal end.

LIST OF REFERENCE NUMERALS h_1=length of the distal part of the picafina, which is sometimes devoid of electrical tips.
h_2=length of the middle part of the picafina, which is populated with electrical tips.
h_3=length of the proximal part of the picafina, which is devoid of electrical tips.
100=body of picafina of our invention.
110_xx_yy=tips/electrical contacts on the surface of body 100. These are the actual neural sensors. xx and yy are indexes for the tips; for example, xx could indicate a set of tips at the same distance from the extremities (or a z-coordinate on a cylindrical coordinate system), and yy could indicate an angular coordinate (or a theta coordinate on a cylindrical coordinate system). In the main embodiment xx takes any value from 01 to 16, while yy takes any value from 01 to 12. As is appreciated by anyone familiar with the art, 12 and 16 are exemplary numbers only, the same principle being valid for any quantity of tips. In particular, our invention allows for many thousands of tips, when the numbers could typically be: radius of tip=0.1 mm (100 micrometers), center-to-center distance between tips=0.2 mm (200 micrometers), 75 tips on the 2.5 mm diameter picafina of FIG. 10, 20 rings equally spaced at 0.2 mm from each other along the z-dimention, on a total 4 mm length along the picafina populated with 1,500 measuring tips. These are possible typical values which do not limit our invention, as any person skilled in the art will notice that such dimensions must be adjusted to each particular application.

810_xx_yy=on/off electronic switch that connect each electrical tip to the common measuring wire(s), also indicated as 810-$x$, when referring to any of the possible switches.

811_xx_yy=on/off electronic switch that connects the signal carrying wires. Can be part of a demultiplexer.

820_xx_yy=timer or pulse stretcher, where xx indicates which "ring" or z-distance, while yy indicates which of the 12 pads in each "ring" in FIG. 10.

830_xx_yy=address decoders for the measuring tips

831_xx_yy=demultiplexers for signal wires that carry the signal from the measuring tips to the proximal end of the picafina. Indexes "_xx_yy" are optional to indicate a particular demultiplexer unless specified "xx" indicating a particular ring or distance from one of the extremities, and "yy" indicating a particular angular orientation around the device with a sequential number running from 1 to the maximum number of electrodes around a particular "ring." Alternatively 831 could also be seen as address decoders selecting one of a plurality of switches, all switches connected to a particular electrode on one side, and each switch connected to one of the plurality of signal carrying wires on the other side. In other words, the demultiplexer can be seen as a combination of an address decoder (or selector) and a bunch of switches that are selected by the address decoder to select one particular way of making the electrical connection.

200=address lines, or address bus
200tip=address lines used for the tip selection
200wire=address lines used for the signal wire selection
210=electrical power wire
211=measurement (signal) wire
212=ground wire

DETAILED DESCRIPTION OF PREFERRED EMBODIMENT

Description of Our Invention

Short, Electrical Engineering Version of Preferred Embodiment

We start with a succinct description suitable for electrical engineers, then follow with a detailed description for wider audiences. The problem that our invention address is to make electric voltage (or current) measurements from internal body parts, as brain, spinal cord, heart or muscles, which may even be not visually accessible. The target point of measurement may also be difficult to locate precisely. To get around the difficulty, or even impossibility, of precisely positioning a relatively small measuring probe next to a desirable, target neuron (for example), that the researcher or the neurosurgeon may not even able to see, our invention discloses a device, here called picafina, which is larger than the hard to locate point of interest. This picafina is then approximately placed in the target location. Such picafina is covered with a multitude of surface electrodes or tips, here called measuring tips, or simply tips, which are of such a size and placement as to cover all the potentially desired points—and more. Given the small size of the tips, as indicated in FIG. 10, and their close proximity to each other, spanning all the potential area of interest, some of the tips 110_xx_yy should be close enough to some of the several or single potential points of interest. After a surgeon inserts such device, the picafina, either the surgeon or a nurse or a technician can select which tips to use, typically by observing the measurements from each tip, one at a time.

Using common techniques of semiconductor and printed circuit board manufacture, it is relatively easy to make a large number (many thousands and more) of relatively small tips (sizes of the order of micrometer or even sub-micrometer) on the surface of the picafina, at its distal extremity, as illustrated in FIG. 10, with the objective of later selecting one or another tip, to precisely control the place where to collect the data, but it turns out that there is a stringent limit on the number of wires that may be pulled inside the picafina to connect these tips to the measuring equipment, because these wires have to go through the limited space available in the body. So, in animals, including human beings, the limited space available for the larger wires limits the number of smaller tips possible to use—each tip needs a wire connecting it to the measuring device. For research with small animals, such as mice, or even insects (Wilson (2004)), current technology can put a many dozen and rarely a few hundreds wires at maximum in the limited available space, therefore a few dozen (or hundreds) tips only can be used (Gregoire Courtine, private communication). To make use of more tips than wires to connect them to an external instrument, the main embodiment of this invention discloses the use of a digital addressing system, which connects one tip at a time to the measuring device. The tip is chosen with the objective of measuring at a particular location, which can be later changed. These locations can be in close proximity, closer than individual tips in prior art could be individually positioned. Jumping from a particular tip to a nearby one, the researcher or neurologist has the possibility of selecting measurement positions with as much accuracy as the tips are apart from each other. Moreover, there is a need to keep more than one tip connected to the measuring device, so this invention discloses a latch which assures that once a measuring tip is connected to the measuring wire, it stays connected even after its address is no longer asserted on the address bus. This aggregate permits the construction of the equivalent of a larger tip, composed of the aggregate of several small tips covering an area as large as needed, up to the total area of all the tips together.

It is envisaged that a signal amplifier (not shown) may exist between the measuring tip 110 and the switch 810 to boost the small signal captured by the measuring tip.

It is also envisaged that switches 810 can be doubled (not shown) for each measuring pad 110, to select whether the pad is connected to a measuring wire or to a ground or reference wire, which can be selected to be near of far from the measuring tip, as needed.

Description of Our Invention

Detailed Version of Preferred Embodiment

A more detailed description of our invention is as follows. FIG. 10 shows a perspective view of a basic version of our invention for a particular main embodiment used for deep brain measurements (say, near de subthalamic nucleus). Starting from the distal extremity (concave, hemispherical extremity in FIG. 10) of the picafina of our invention, and following now only the external features of it, there is a solid, smooth and concave part of length h_1=2.5 mm (typical value), on the surface, inside of which there is no useful feature. Continuing on the z-dimension towards the proximal, flat extremity, next comes the part populated with the electrical tips, on a length h_2=25 mm. In the inner part of it there are wires and electronics described in the sequel. This is followed by another smooth part on a length h_3=45 mm, for a total length h_total=72.5 mm. These are typical values, see FIG. 10, for insertion in the brain of a human animal; for measurements in other parts of a human animal, or for measurements in other animals of different size, the sizes have to be adjusted as needed, without detracting from the disclosure of the invention. Inside this distal part h_2 runs wires as described in the sequel. The distal end h_1 is shaped as indicated in FIG. 10 to facilitate the insertion of the picafina into the mush brain tissue, while the proximal end (near the skull) is flat to facilitate the electrical connections and mechanical sealing. Other affixing features, as tapped holes for screws at the flat proximal end and equivalent features are not shown for simplicity. At the picafina's proximal end there are a number of wire endings with the necessary means for connection to extension wires. In this main embodiment there is only one measurement wire 211 (voltage measurements), one power wire 210 (to bring power to the electronics inside the picafina), one ground (return) wire 212 and a plurality of address wires 200 (8 in this main embodiment). As known to the practitioners of the art of electronics more than one return wire may be used to avoid ground loops.

The picafina's outer surface is made of some material compatible with human tissues, e.g. polyurethane (for the bulk) and titanium (for the measuring metallic tips) in the main embodiment. These materials are only used as examples used in current art picafinas, many other materials being possible, and the particular material being irrelevant for our invention. The body has to be of a material that does not conduct electricity, while the tips or measuring pads are made of a material that is a good electrical conductor, e.g., a metal. The tips are to serve as contact points of electrical currents somewhere in the body, which, for the main embodiment is deep inside the brain.

The dimensions indicated in FIG. 10 were chosen for simplicity of description, particularly the number of measuring tips, which is chosen low to make the analysis simpler and the features visible in the drawing. In this main embodiment described here there are 192 measuring tips, numbered not sequentially but accordingly to the rings they belong as 110_01_01, 110_01_02, 110_01_03 etc, until 110_01_12, for the 12 most distal tips (i.e., on the most distal ring of tips), then 110_02_01, etc. for the next ring, etc. until the most proximal ring of tips, which is numbered 110_16_01, etc., in FIG. 10. In the main embodiment these tips are made of titanium. These tips are to be the initiation points to electrical contacts with nearby cells—neurons in this case. With the indicated dimensions, typical tip diameter is 0.654 millimeters and edge-to-edge separation is also 0.654 millimeters along the circumference, so center-to-center separation between the tips is 1.309 millimeters along any circumference at a fixed distance from any of the ends (fixed z dimension). On a 5 mm. diameter picafina, there are 12 such tips on a circle, only the 6 on the visible side being seen on FIG. 10, at any particular distance from any of the ends, there existing other 6 tips on the back, invisible side. Along the z coordinate the separation between pads is also 1.309 mm (typical dimension), making 16 such circles populated with 12 tips each, making a total of 192 tips on a z dimension length approximately equal to 20 mm (h_2). These are possible dimensions, in no way to be taken as restricting our invention, as many other values being compatible with our invention, as known to the ones skilled in the art. The number of tips displayed in the drawing was chosen to be only 12 on any circumference so as to make the drawing clearer, a typical picafina having 10 to 100 or more times more measuring tips on any of the rings in h_2 in FIG. 10.

Referring again to FIG. 10, describing now the inner structure of the picafina 100, also starting from the distal end of it (the concave extremity), the first 2.5 mm of it (h_1, typical dimensions) have no features inside. In the particular preferred embodiment, said distal end is solid and made of the same compatible material as the external surface of the picafina. Moving towards the proximal end of the picafina, at the distance h_1=2.5 mm. from said distal end (see FIG. 10), there is at the surface a first set of electrical contacts or tips, 110_01_yy (yy running from 01 to 12), along an imaginary ring on its outer surface. These electrical tips are connected to electrical circuits inside de picafina, which are described below. FIG. 7a is a conceptual drawing of a cross section of the picafina of our invention, made perpendicular to the long, or z dimension shown in FIG. 10, made at a distance approximately 2.5 millimeters from the distal end, that is, at the plane containing the ring of electrical tips closest to the picafina's distal end. What is shown in FIG. 7a is not a drawing of the transistors and other electronics devices as they are seen in a microscope, but a symbolic representation of the electronics at that position, the actual transistor construction being out of the scope of the invention, not included in the invention, and part of the old art of semiconductor and printed circuit board manufacture. The transistors themselves do not even have to be in a single plane, but are stacked as needed for connections among them. While FIG. 7a depicts a schematic (simplified) view of the electronics circuits that determine our invention, FIG. 7b shows in more detail the electronics for one single electrical tip, one of the 12 repeated circuits around the circle at FIG. 7a. Each tip is connected by a similar electronics circuit to the signal carrying wires, though varying in the address, as each tip has its own dedicated address. These two figures best display the innovation over prior art brought by our invention, as they show the method which allow the use of much larger number of electrical tips than prior art, and the reader is requested to pay special attention to these and its description. FIGS. 7a and 8a only show the general features of the circuits and their interconnections, while the details of the circuits are shown at FIGS. 7b and 8b. Referring to FIGS. 7a and 7b, each of the address decoders 830_xxyy contains a unique address written in it. Moreover decoders 830 are such that their outputs are high when the address at address bus 200tip is equal to the particular, unique address written in said particular decoder 830, which is the tip address, and low otherwise. Therefore, when address for tip 110_01_01 is asserted on the address bus 200tip, that is, when 200tip has value (0000 0001) the address decoder 830_01_01 recognizes the address and makes its output to go high, while none of the other address decoders recognizes the address as theirs, so all other address decoders keep their outputs low. This in turn causes the electronic switch 810_01_01 to be turned on, connecting tip 110_01_01 to the measurement wire and to the measuring instrument. Writing a different address on address bus 200, for example, (0000 0100 digital=04 hex=04 decimal), causes another address decoder to select another tip for measurement. In the main embodiment, 8 address lines can create 2 power 8=256 different addresses, enough for the 196 tips in it, so 8 address lines are enough.

It is envisaged that the main embodiment may also have a latch (not shown) for each output of the decoders 830. With such latch it is possible to have more than one tip 110 connected to the measuring wire at the same time, in effect creating an average or integrated measurement among several tips. Among other possibilities is to connect a large number of adjoining tips to create an effective larger area tip, thereby increasing the signal strength.

FIG. 7b shows the electrical connections between the main conceptual blocks disclosed in the main embodiment of our invention. FIG. 7a shows a cross section of the picafina of our invention taken perpendicular to its longer, or z-dimension, and FIG. 7b shows these connections isolated from the body 100. Is shows the address decoders 830, the electronic switches 810, the measuring tips 110, the wiring for them, the address bus and the power and the measurement wires. The twin electronic switch 810 for selection of the ground or return wire is not shown, for simplicity. Any measuring tip may act as either signal or return/reference tip. Return tips may be omitted, in which case the reference may be taken as the full cell assembly, of animal body.

FIGS. 9a and 9b shows possible implementations of address decoder 830 with inverters and AND gates. FIG. 9a shows a decoder for addresses 0001B=01D=01H and FIG. 9b shows a decoder for address 1100B=12D=0CH (binary, decimal and hex representations). Each measuring tip has a particular combination of inverters that determines its particular address. These circuits are made using the standard techniques of semiconductor fabrication. This is only an exemplary version, many other possibilities existing for address decoders, which is a mature field in digital electronics, not part of our invention. In the preferred embodiment of our invention said address decoder is also grown on the substrate of each layer that serves a particular set of tips 110_xx_yy at a fixed distance from the ends of the picafina, for example, the 12 tips described above, part of the most distal "ring" of tips.

Returning to FIG. 7a it shows the electronic circuits existing at that cross section, not necessarily at their exact position, as the positioning of the electronic parts is not part of our invention, but only their function and logical connection. The detailed implementation of the electrical connections are known in the art of electronics. In particular the actual transistors and electrical connecting wires most likely will in practice be not on a single plane but on different layers, according to the established art of transistor and printed circuit board manufacture. Rather, FIGS. 7a and 7b and its details are intended to show the logical connections among the devices, which will be implemented according to the established art of die and printed circuit manufacture, the actual implementation of the circuits being part of the established art. Both transistor and printed circuit boards are mature fields on which our invention makes no improvements. Our invention works with this electronics that are described in this layer or some of its electronics equivalents.

For the main embodiment described, which has 16 "rings" of tips, each at a different z-coordinate and with 12 tips each, there are 16 group of circuits similar to the circuit described above for the most distal "ring", except for the addresses, which is unique for each tip.

Between each plane of electronics there are vertical "wires", which in this case are made using the established techniques of semiconductor manufacture or of printed board manufacture, or a combination of these, such "wires" connecting all the 8 address lines 200, the "wire" 210 that carries the electrical power to the electronics, the "wire" 211 that connects the selected tip to the external measuring instrument and the "wire" 212 for ground and possibly an extra wire for latching and for separate ground or return (not shown in FIG. 7). Such vertical wires connecting in parallel all 16 planar set of circuits described above continue beyond the most proximal layer of measuring tips 110_16_yy to the proximal end of the picafina, where they end at the connectors for wires 200, 210, etc. shown at FIGS. 10 and 4b.

Said wires running inside the picafina of our invention are, in the preferred embodiment here described, constructed with some combination of semiconductor manufacture, printed circuit technology and manual soldering. For example, all the address decoders 830 and the switches 810 that serve a particular set of tips at a fixed axial distance from the ends of the picafina (say tips 110_01_01 through 110_01_12) could be made of current technology of semiconductor manufacture, and their connection to each of the tips could be individually made by a technician at fabrication, while some of the vertical connections from layer to layer could be made with vias and the existing technology of printed circuit manufacturing, while others vertical connections with the technology of semiconductor manufacture. But printed circuit technology, or semiconductor manufacture, or manual soldering are not intended to be restrictive for our invention, any other equivalent technology or any combination of them being acceptable.

From the connectors shown at the proximal end of the picafina at FIGS. 10 and 4b, wires of the necessary length (not shown) connect the proximal end of the picafina to the electrical power supply, the control and measuring instruments. The control and measuring instruments can be as simple as manual switches to set addresses and ordinary voltmeters that need a human to read the value, to sophisticated computer controlled instrumentation (see FIG. 11).

It is envisaged that a an amplifier may exist between the measuring tip 110 and the switch 810 to amplify the weak signal captured at the measuring tip.

Operation of Invention

Preferred Embodiment

Similarly to the description of the invention we start with a disclosure of the operation written for electrical engineers and in a succinct form, followed by a detailed explanation of the operation.

Operation of Our Invention

Short, Electrical Engineering Version

In a main embodiment, one of a large number of measuring tips is selected for connection to a single measuring wire connecting to the measuring instrument (e.g., a voltmeter), with an address bus. An address bus with n lines can select up to 2 power n individual measuring tips. The researcher or neurosurgeon inserts the picafina described above in the general area where he/she wants to make measurements, then selects which measuring tip to use asserting the appropriate address in the address lines. Once a particular measuring tip is selected, all the measurements indicate the voltage at that particular location. The measuring tip can be changed later, as needed. More than one tip can be selected concurrently making use of latches that keeps a tip selected even after its address is changed, and an extra deselect line is capable of turning off all switches at once.

Operation of Our Invention

Detailed Version

The invention is a method and a means to make a very large number of measuring tips, each usually being of smaller physical size when compared with prior art, to make precisely located electrical measurements on neural and muscle tissues. The measuring tips smaller size and closer proximity to each other, when compared with previous art, is part of our invention. The researcher or the neurologist/neurosurgeon need only to insert the picafina of our invention on the general vicinity of the area of interest, which is in itself an improvement over prior art, which required more precise positioning of the electrode tips than our invention does. Once the picafina is positioned in such a way that the area covered by the electrode tips (h_2 in FIG. 10) is in the general position on which measurements are to be made, the precise measuring point is chosen selecting one out of the many tips covering the target region and more. This is made with the address lines 200 that control address decoders 830. For the main embodiment of our invention, address lines 200 of decoders 830 are used to close the connection of one and only one electrode measuring tip to the wire that is connected to the measuring instrument. This is done as follows:

The address lines 200 that control address decoders 830 are in such a number as to be able to create unique addresses for all the electrode tips on the particular picafina. For the main embodiment here described, with a small number of measuring tips for simplicity, 196 electrode tips, there is a need of 8 wires (making 8 bits), which can make up to 2 power 8=256 different addresses. In the main embodiment, the address is externally chosen with a set of 8 DPDT switches, each switch connected at the proximal end of the picafina to one of the eight address lines for decoders 830, with which each of the 8 address lines can be made either high or low as desired, therefore creating each of the 196 necessary addresses. Such a manual selection is only one of the possibilities, it being appreciated by the practitioners of the art that automatic selection can be made, e.g., using a programmable computer or similar means. The addresses are created with the ordinary binary number system, as known to the practitioners of the art of digital electronics. If an address is put on an address line 200 that does not correspond to any actual measuring tip, then no tip is connected and nothing happens. Once a particular address is created with said switches (for example, 0000-1010B=0AH=10D), if said address corresponds to one of the existing addresses of the many address decoders 830, (decoder 830_10_01 for example) the address on bus 200 will be recognized by its corresponding address decoder 830_10_01, which will respond changing its output from low to high, which in turn will change the electronic switch 810_10_01 that is associated with it to the "on" state, connecting the measuring tip associated with that particular address decoder to the measuring wire. From this time on the measuring instruments will be measuring the voltage at the vicinity of measuring tip which corresponds to address 10D, indicated at FIG. 10.

The measuring wire is connected at the picafina's proximal extremity to a measuring instrument, which in the main embodiment is a voltmeter with scales capable to measure millivolts and microvolts.

The selection of measuring tip can be made from a computer program, which typically has a "feeling" similar to the standard graphic interfaces, as, for example, shown in FIG. 11 which, nevertheless, was drawn for the more complex embodiment described below. Such a program may be called a DPU (Doctor's Programming Unit), for example.

Description and Operation of Alternative Embodiments

Second Embodiment of Our Invention

Description of the Invention

Description of Second Embodiment

Short, Electrical Engineering Version

A second embodiment discloses the use of multiple signal wires to carry the signal from the picafina surface to an external measuring instrumentation (e.g., a voltmeter) and a separate second digital addressing system to select which of said wires is connected to the selected measuring tips. The electrical connections for this second embodiment are shown in FIG. 8a and FIG. 8b. Said second digital addressing system is separate from the first digital addressing system only logically, as each is a set of wires running in parallel. Each of the available wires to carry the signal can be connected to any of the available measuring tips, allowing several simultaneous measurements from different measuring tips, as many as there are signal wires. In this embodiment, at the same time that a measuring tip is selected, the output of its address decoder 830 besides closing (turning on) the electronic switch 810 associated with the tip that corresponds to itself, also performs two functions. Firstly it enables a demultiplexer or second address decoder 831, that selects one of the signal carrying wires to connect the selected measuring tip to one of the available signal connecting wires—the signal connecting wire selected by said second address bus (see FIGS. 8a and 8b). Secondly it sets the system to latch the selected switches, so that this particular combination of measuring tip+signal carrying wire will stay connected even after the address bus changes to select another combination. These latches are not shown in the figures as they are internal part of the switches. Also, as is typical with latches, they can be released (going to off state). In this case a common wire carry an unlatch signal to all latches in the picafina of our invention (not shown). It is intended that the number of connecting wires is much smaller than the number of measuring tips. Once the addresses for a particular measuring tip and for a connecting wire are selected, these addresses are stored in local memory (latched), freeing both address buses to assert other addresses. Alternatively address decoder 831 together with switch 811 can be seen as a demultiplexer.

Description of Second Embodiment

Detailed Version

The second embodiment of our invention uses two address buses 200; 200tip for the measuring tips, and 200wire to select one of a plurality of connecting wires. This alternative embodiment offers the possibility of having several separate wires connecting several different measuring tips to external recorders working in parallel. Any measuring tip can be connected to any of the signal measuring wires. In this embodiment the number of measuring tips is still very large, say a few thousands, with a smaller number of connecting wires, say a dozen to a few hundreds. In this embodiment, concomitantly to selecting a particular measuring tip with decoder 830, say 110_10_01, the user sets another address in another independent address bus 200 wire, which is decoded by another address decoder/demultiplexer 831 (FIGS. 8a and 8b), which selects a particular connecting wire to carry the signal captured by tip 110_10_01 to the proximal end of the picafina and from there to the voltmeter or other measuring instrument. In this embodiment there is a latch associated with both electronic switches 810 and the implied internal switch in 831 because both the measuring tip and the connecting wire have to stay selected even after the address buses 200 (200tip and 200wire) have have other address values for other combinations.

Consequently this second embodiment of our invention extends the use of the addressing system to the selection of one connecting signal wire from a plurality of wires available throughout the body of the picafina, each one capable of connecting any of the measuring tips with the proximal end of the picafina of our invention, from which they can be extended by ordinary means to the measuring instrumentation, e.g., voltmeters. FIGS. 8a and 8b shows the electronic connections and parts. Measuring tip 110 is connected via a first digitally controlled switch 810, which turns on/off under the control of a first address decoder 830, to a demultiplexer (which can be viewed as a combination of an address decoder 831 and a plurality of switches 811), to one of the signal connecting wires that runs inside the picafina to the proximal end of said picafina, from which connection is made as required to a reading instrument, as a voltmeter. Once either address bus selects an address for either the measuring tip 110_xx_yy or for the signal wire 211_zz the selection is latched and stay latched until a signal is send to another wire, not shown, which has the appropriate circuitry to unlatch all the latched addresses, which can be used to select new measuring tips and new connecting wires with a new selection cycle. The combination address decoder 831 and switch 811 can be seen as a demultiplexer.

Second Embodiment of Our Invention

Operation of the Second Embodiment

To operate the second embodiment the user must start resetting all the latches to the off state, which the user does with the latch off signal (not shown). He/she then starts selecting the first address for the measuring tip he/she needs in the same way as is done with the main embodiment, e.g., with individually set switches, or with a decoding pad, or with a microcomputer or any equivalent way as known to the practitioners of the art to assert the required addresses at the appropriate address buses, then, at the same time (concomitantly) the user also selects the address for one of the available connecting wires 211_zz which run inside the length of the picafina of our invention. In the particular electronic design shown for the second embodiment both addresses have to be selected concomitantly because in this second embodiment the address bus that selects a particular surface measuring pad also enables the address decoder that selects which signal carrying wire is chosen, so that the signal connecting wire is connected only to the selected measuring pad, but alternative designs are possible, in which the selection is made not at the same time, still implementing the same principles, this being only one possibility for implementation. Address decoder 830 being selected for that particular measuring pad, the latches are on for its electrical measuring pathway, so the combination will latch and will stay closed after the address bus is changed to select another combination measuring tip+ signal measuring wire. With this, the user has completed the connection from the selected measuring tip to a single, identifiable wire at the proximal end of the picafina of our invention. The user selects then a second measuring tip 110 and a second connecting wire 211 in the same manner as the previous one, then a third and so on, until he/she selected all the desired measuring points using one of the available connecting wire for each measuring tip. As described elsewhere, it is also possible to connect said second measuring tip 110 to the same connecting wire 211, or any number of measuring tips, wherein the effect is to create a virtual measuring tip with a larger area, which increases the current or the strength of the signal captured. When all the measuring tip selections are made and the connecting wires 211 have been connected to the external measuring instruments the user is ready to acquire data. Several voltage measurements can be taken in parallel with this second embodiment, for example, to study firing correlation between neurons.

A Doctor's Programming Unit (DPU) may be used to make these selections, as shown in FIG. 11 for a simplified case of fewer measuring tips and fewer signal carrying wires as a typical picafina is supposed to have.

Another alternative embodiment is the addition of a buffer amplifier between the measuring tip and the electronic switch 810 (not shown). One of the advantages of such buffer amplifier is to obviate the know problems of building an electronic switch 810 with no voltage drop across itself, which is particularly important when the signals to be measured by measuring tips 110 are very small. Such a first end amplifier could be critical to measure the small voltages propagating along the neurons, captured by measuring tips 110.

Still another alternative embodiment is to have a summing amplifier (not shown) between the measuring tip 110 and the electronic switch 810. Such summing amplifier should receive at a first input the voltages at the measuring tip 110, and at a second input a fixed DC constant voltage V_bias that may derive from either an external or internal source. In such an embodiment the electronic switch 810 receives its input at a high enough electric potential not to pose constraints on its design due to voltage drop across said switch 810.

Still another alternative embodiment is to bias the input of the electronic switch 810 (not shown), which must then be blocked from inserting current on the neurons being measured by an isolation capacitor (not shown) between said DC and the measuring tip 110.

Still another alternative embodiment of our invention (not shown in figures) is the use of radio signals to create the addresses for the address decoders (and/or the addresses for the signal wires on the first alternative embodiment). In this embodiment there is no physical address wires connecting the distal end of the picafina with the user (researcher or neurologist). Any radio communication link is feasible, over the EM spectrum, including, e.g., microwaves etc., and such action-at-a-distance information is sometimes referred to as telemetry. This invention does not include a new radio communication system, but simply use existing telemetry devices. In this alternative embodiment the connecting wires for the address bus 200 and 200wire are substituted by a telemetry unit inside the picafina of our invention, which receives the addresses sent by the user using a transmitting unit. Once received, the addresses are stored in memory physically located at the distal end of the picafina, near the measuring tips, said storing memory taking the place of the connecting wires. Such an alternative embodiment decreases the number of wires connecting the picafina with the outside world, which may be important when taking measurements on small animals, as in a mouse or even on an insect, when it may be advantageous to use smaller wires connecting the animal to the controlling and measuring instruments.

Still another alternative embodiment of our invention is a battery operated device (not shown in figures) which have the advantage over the main embodiment for chronical implants (long-term implants), which are devices that are expected to stay on for several months or even years. In this case it may be better to have the ability to have a battery operated, self-contained electrode system that is capable to receive orders by telemetry link and also send results out to an external receiver also by telemetry link. This alternative embodiment obviates the need to have the animal continuously attached to a wire, particularly because it is difficult to prevent the animal from scratching the point of penetration of the wire, with subsequent destruction of the connection and perhaps starting an infectious process. In this variation, though the implanted device is no longer physically accessible after the surgery, its electrical properties can be adjusted and changed via radio or magnetic or other type of action-at-a-distance communication. For example, the telemetry link may be an ordinary electromagnetic link between the picafina of our invention and a programming unit that transmits information to the picafina. This telemetry link may work in the same technological principles as a cell phone, or a cordless telephone, or a wireless computer mouse or a wireless computer keyboard, or a remote control used for TV, CD, DVD or similar household devices. Some of these use infra red communication, which has limited range in implanted devices because of infra red radiation absorption in tissues, others use FM or other electromagnetic "radio" waves, which have more transmission through bodies than infra red radiation does, and the ones that use "radio" waves use a variety of frequencies, each one with its own advantages. Depending on the size of the animal and implant depth one or other of these will be more advantageous over the others. The particular type of telemetry, and the electronics to implement it as well, are not described here because telemetry and electronics are old arts. In this alternative implementation after surgical implant and after the necessary period of healing, the electrode tip addresses are selected by transmitting the information by telemetry (radio, etc.) to the implanted unit, which subsequently sends the information out by radio telemetry also.

Still another alternative embodiment of our invention is to have the output of the address decoder latched, that is, it continues forever in the high state when it is selected until a deselect signal is asserted. Many addresses can be chosen at the same time.

CONCLUSION, RAMIFICATIONS, AND SCOPE OF INVENTION

Thus the reader will see that the electrode measuring tips of the invention provide a highly reliable device which offers the advantage over prior art of being able to make electrical measurements on more precisely located points on the vicinity of nerves and other cells inside living organisms. The smaller dimensions of the measuring electrodes (tips) of our invention allow for more precise measurements from a single neuron, instead of average measurements from several neurons that happen to be near a larger measuring tips or probes of prior art. At the same time, our invention permits the measurements from several tips in parallel, which tips can be adjoining to each other, making the equivalent of a larger tip of prior art. These options give more flexibility and options to the user of our invention. Also prior art used measuring tips at the end of a dedicated physical support which both forced a larger than necessary physical distance between these measuring points, which in turn caused the absence of measuring points where potentially needed (between two tips), as well as increased trauma to the organism, as each tip was the origin of a penetrating sharp object at the end of which it sat. Moreover, the electrode measuring tips of our invention allows for changing measurement position from points separated by a few micrometers, or the distance between each tip, without moving the supporting structure (the picafina). This possibility of changing the measuring tip to be used while keeping the picafina of our invention in the same place is important, as each repositioning involves trauma to the animal. Moreover, the change from one tip to the other is also important, because the distance between the tips can be made very small, a few micrometers with modern technology of semiconductor and printed circuit board (PCB) manufacture, which is much smaller than the separation between tips in multi tip measuring devices in current use. Therefore the picafina need not be positioned with accuracy with respect to any neuron or other body cell, and the possibility of adjustments of the measuring position switching from one tip to another nearby tip is equivalent to micropositioning the measurement site, or to make small changes on the measurement site.

The wires at the proximal end of the picafina of our invention do not have to be grouped as indicated in the main embodiment, any other grouping being acceptable, as the grouping does not alter the working of our invention. For example, all the wires could end on a single harness, or each wire could have its own dedicated connector, or any combination of these, because the particular form of connecting the wires are not part of this invention.

The wires or cables at the proximal end of the picafina of our invention may be duplicated (redundant wires), as shown at FIG. 12, so that the picafina of our invention can still be used if one of the wires happens to break, simply changing to its backup wire or cable.

The measuring tips can be of any shape different of the circular shape indicated in the main embodiment without altering the scope of the invention. For example, the measuring pads can be square shaped, as indicated in FIG. 2, or they can be elongated, as shown at FIG. 3, or they can be in the shapes shown at FIGS. 5*a* and 5*b*. These variations and many others are possible and fit particular applications, none of them expressing any intrinsic variation from our invention.

The very body of the picafina of our invention can have shapes other than cylindrical. FIGS. 6*a* and 6*b* show two such possible variations. Variations on the shape of the picafina of our invention to adapt to specific applications do not constitute an intrinsic variation of our invention and are covered by this patent. It is envisioned that a flat surface may be useful in many cases, due to the layered structure of the brain.

The distal interior part of the picafina described in the main embodiment is solid and made of the same material as its surface, but this is not necessary, it being possible to have a hollow interior, or an interior made of a different material then the exterior surface, this detail not affecting the working of the invention as it will be seen by the persons familiar with the art.

The address decoders 830 that turns on/off the switches 810, thereby connecting the measuring tips 110 can be as simple as a digital (or binary) comparator, for example the National Instruments 54AC520 or the Texas Instruments 5962-8681801RA, or some other more complex circuit, or even a especially designed electronic circuit, the particular nature of the address decoder not impacting our invention, but only that it recognizes that the address asserted in the address bus 200 is the same as the address assigned to the contact that it is supposed to turn on/off.

While our above description contains many specificities, these should not be construed as limitations on the scope of the invention, but rather as an exemplification of one preferred embodiment thereof and a few typical variations. Many other variations are possible. For example the cross section of the picafina of our invention can be of many other shape, as elliptical or rectangular, some of which are shown in FIGS. 6a and 6b. Besides elliptical and rectangular, it can be of any irregular shape, or the cross section can even vary along the long dimension of the picafina. The measuring tips do not have to be flush with the picafina's body, but can be either protruding out of it or be recessed onto it. The protruding tip could be made with the nanotechnology. The dimensions suggested for the main embodiment are intended for a picafina designed to make measurements deep in the brain of a human animal; these dimensions are necessarily different when the intended animal is not a Homo, but a smaller mouse or an even much smaller insect, or for measurements at the brain cortex, for example, which is located just below the skull, or for measurements on the spinal cord, or from other neurons or other cells on the heart, intestines, or any other organs or extremities like arms. The measuring tips can be made of metals other than titanium, such as platinum, vanadium, iridium, silver, gold, surgical steel, stainless steel, MP35N, platinum-iridium, amalgams, alloys, and combinations, among others. and the body can be made of other insulators other than silicon, such as polyurethane, polyethylene, polyimide, polyvinylchloride, PTFE, ETFE, ceramics, various biocompatible polymers, or combinations of these, among others.

The connections inside said picafina are made with any of the technologies developed for printed circuits and/or chip manufacture (integrated circuits or IC). For example, both the subtractive and the additive processes used in printed circuit manufacture can be used to print the connecting power and address lines. The integrated circuits and transistors shown as a block diagram, for example, at FIG. 7 could be made with the ordinary technology used for chip manufacture, as well as some of the wires that interconnect them and/or wires that connect them with the main connecting wires along the picafina. It is also possible to use a combination of these, some connections using the printed circuit technology, other using the smaller IC technology, the particular choice depending on the size and complexity of the particular picafina.

Accordingly, the scope of the invention should be determined not by the embodiment(s) illustrated, but by the appended claims, drawings and invention description, and their legal equivalents.

REFERENCES

Gregoire Courtine (2008): Courtine Gregoire Courtine, private communication (Jun. 3, 2008)
GREGOIRE COURTINE, Ph.D.
Prof. Dr. Gregoire Courtine
Division of Psychiatry Research
Experimental Neurorehabilitation Laboratory
August Forel-Strasse 7
CH-8032 Zurich
Cruikshank (2008): Scott J. Cruikshank & Barry W. Connors "Neuroscience: State-sanctioned synchrony", Nature 454, 839-840 (14 Aug. 2008)
Donoghue (2007): Donoghue et al. U.S. Pat. No. 7,212,851 "Microstructured arrays for cortex interaction and related methods of manufacture and use" May 1, 2007
Irazoqui-Pastor (2008): Irazoqui-Pastor, et al. "Wireless neural data acquisition system" U.S. Pat. No. 7,346,312, Mar. 18, 2008
Jenkins (2006): David Jenkins et al. "Medical implant device for electrostimulation using discrete micro-electrodes" U.S. Pat. No. 7,096,070, Aug. 22, 2006
Kandel (2000): E. Kandel, J. Schwartz, and T. Jessell, "Principles of Neural Science" 4$^{th}$ edition (2000)
Medtronics (n/d): http://www.medtronic.com/physician/activa/surg_components.html
Nicolelis (2008): Miguel A. L. Nocolelis "Methods for Neural Ensemble Recordings" (2$^{nd}$ ed.), CRC Press (2008)
Nicolelis (1998): Nicolelis M A, Ghazanfar A A, Stambaugh C R, Oliveira L M, Laubach M, Chapin J K, Nelson R J, Kaas J H. "Simultaneous encoding of tactile information by three primate cortical areas", Nature Neurosci. 1998 November; 1(7):621-30. http://www.ncbi.nlm.nih.gov/pubmed/10196571?ordinalpos=1&itool=EntrezSystem2. PE ntrez.Pubmed.Pubmed_ResultsPanel.Pubmed_ DiscoveryPanel.Pubmed_Discovery_RA& linkpos= 5&log$=relatedarticles&logdbfrom=pubmed
REF_Pouget Reed J L, Pouget P et al., Widespread spatial integration in primary somatosensory cortex. Proc Natl Acad Sci USA. 2008 Jul. 22; 105(29):10233-7. Epub 2008 Jul. 15, expected publication Jan. 22, 2009
Poulet (2008): James F. A. Poulet & Carl C. H. Petersen "Internal brain state regulates membrane potential synchrony in barrel cortex of behaving mice" Nature 454, 881-885 (14 Aug. 2008)
Wilson (2004): Rachel J. Wilson, G. G. Turner and G. Laurent "Transformation of olfactory representations in the Drosophila antennal lobe", Science 303, 366-370 (2004)

What is claimed is:

1. A picafina device for measuring an electrical signal occurring in body cells, the device comprising:
    a generally cylindrical device body with a proximal extremity, a distal extremity, an inner lumen and an outer surface;
    an anchor at the distal extremity;
    a plurality of measuring electrode tips on the outer surface in fixed relative positions at the distal extremity and on the anchor;
    a single signal carrying wire running inside the lumen;
    a plurality of electrode tip connectors in the distal extremity, each connector for connecting one of the measuring electrode tips to the signal carrying wire;
    a plurality of on/off switches, each on/off switch associated with one of the measuring electrode tips for selecting the associated measuring electrode tip and connecting it to the signal wire; and
    a device connector at the proximal extremity to connect the signal carrying wire to additional wires outside the device body, the additional wires for connecting to a measuring and/or recording instrument;
    wherein the measuring electrode tips are configured to measure the voltage values at cells next to the respective tips.

2. The device of claim 1 further comprising a plurality of electrical amplifiers, each electrical amplifier between each one of the measuring electrode tips and associated on/off switch.

3. The device of claim 1 further comprising a means for connecting several of the measuring electrode tips in parallel to the signal wire, said means capable of latching the on state of each on/off switch.

4. The device of claim 1 further comprising a timer electronic circuit that controls the length of the "on" time of the on/off switches such that once one of the plurality of switches is turned "on" it is kept in the "on" state for a pre-determined time, after which the timer electronic circuit moves the switch to the "off" state.

5. The device of claim 1 further comprising:
an addressing means having bits to uniquely address each of said measuring electrode tips; and
a plurality of address decoders, wherein each address decoder is for one of the measuring electrode tips and associated on/off switch and each address decoder having a unique digital address;
wherein the address asserted on the addressing means at the proximal extremity is compared to the unique digital addresses of the address decoders such that when the unique digital address is equal to the asserted address, the address decoder causes the associated on/off switch to enter the "on" state, thereby completing the electrical connection between the measuring tip and the single signal wire in order to record voltage levels at the cell next to the measuring tip electrode.

6. The device of claim 5 wherein the addressing means further comprises a wire running parallel to the signal carrying wire inside the lumen.

7. The device of claim 5 wherein the addressing means further comprises a wireless telemetry circuit.

8. The device of claim 5 further comprising a timer electronic circuit that controls the length of the "on" time of the on/off switches such that once one of the plurality of switches is turned "on" it is kept in the "on" state for a pre-determined time, after which the timer electronic circuit moves the switch to the "off" state.

* * * * *